(12) United States Patent
Nanko et al.

(10) Patent No.: US 11,639,330 B2
(45) Date of Patent: *May 2, 2023

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Masaki Nanko, Ichihara (JP); Naoya Fukumoto, Ichihara (JP); Daisuke Yagyu, Ichihara (JP); Yuta Yamaguchi, Kawasaki (JP); Tsuyoshi Kato, Ichihara (JP); Hiroyuki Tomita, Ichihara (JP); Katsumi Murofushi, Ichihara (JP); Shohei Nishizawa, Ichihara (JP)

(73) Assignee: SHOWA DENKO K.K., Tokyo (JP)

( * ) Notice: Subject to any disclaimer, the term of this patent is extended or adjusted under 35 U.S.C. 154(b) by 586 days.

This patent is subject to a terminal disclaimer.

(21) Appl. No.: 16/640,132

(22) PCT Filed: Jul. 30, 2018

(86) PCT No.: PCT/JP2018/028455
§ 371 (c)(1),
(2) Date: Feb. 19, 2020

(87) PCT Pub. No.: WO2019/039200
PCT Pub. Date: Feb. 28, 2019

(65) Prior Publication Data
US 2021/0188766 A1   Jun. 24, 2021

(30) Foreign Application Priority Data
Aug. 21, 2017   (JP) .............................. JP2017-158650

(51) Int. Cl.
*C07C 255/13*   (2006.01)
*G11B 5/725*   (2006.01)
(Continued)

(52) U.S. Cl.
CPC ........ *C07C 255/13* (2013.01); *C07C 43/2055* (2013.01); *C07C 255/17* (2013.01);
(Continued)

(58) Field of Classification Search
CPC ............ C10M 107/38; C10M 2213/00; C10M 2213/04; C10M 2213/043; C10M 2213/06;
(Continued)

(56) References Cited

U.S. PATENT DOCUMENTS

| 4,360,645 A | 11/1982 | Krespan et al. |
| 4,526,833 A | 7/1985 | Burguette et al. |

(Continued)

FOREIGN PATENT DOCUMENTS

| CN | 1705698 A | 12/2005 |
| CN | 102639477 A | 8/2012 |

(Continued)

OTHER PUBLICATIONS

First Office Action dated May 7, 2022 issued by the Chinese Patent Office in Chinese Application No. 201880053594.9.
(Continued)

*Primary Examiner* — Holly Rickman
(74) *Attorney, Agent, or Firm* — Sughrue Mion, PLLC

(57) ABSTRACT

Provided is a fluorine-containing ether compound that can be suitably used as a material for a lubricant for a magnetic recording medium, capable of forming a lubricant layer having excellent chemical substance resistance and wear resistance even when the thickness is small. A fluorine-containing ether compound represented by the following formula (1):

(Continued)

$$R^1-R^2-CH_2-R^3-CH_2-R^4-R^5 \quad (1)$$

In the formula (1), $R^3$ is a perfluoropolyether chain. $R^2$ and $R^4$ are divalent linkage groups having a polar group, and may be the same or different. $R^1$ and $R^5$ are terminal groups bonded to $R^2$ or $R^4$, which may be the same or different, and at least one of $R^1$ and $R^5$ is an organic group having 1 to 8 carbon atoms wherein one or more hydrogen atoms of the organic group is substituted with a cyano group.

11 Claims, 1 Drawing Sheet

(51) Int. Cl.
*C07C 43/205* (2006.01)
*C07C 255/17* (2006.01)
*C07C 255/19* (2006.01)
*C07C 255/50* (2006.01)
*C07D 333/16* (2006.01)
*C08G 65/08* (2006.01)
*C10M 107/38* (2006.01)
*C10N 40/18* (2006.01)

(52) U.S. Cl.
CPC .......... *C07C 255/19* (2013.01); *C07C 255/50* (2013.01); *C07D 333/16* (2013.01); *C08G 65/08* (2013.01); *C10M 107/38* (2013.01); *G11B 5/7257* (2020.08); *C10N 2040/18* (2013.01)

(58) Field of Classification Search
CPC .......... C10M 2213/0606; G11B 5/725; G11B 5/7257; C10N 2040/18; C08G 65/333; C08G 65/08; C07C 255/13; C07C 43/2055; C07C 255/17; C07C 255/19; C07C 255/50
See application file for complete search history.

(56) References Cited

U.S. PATENT DOCUMENTS

| | | | |
|---|---|---|---|
| 5,157,066 A | 10/1992 | Shoji et al. | |
| 5,221,494 A | 6/1993 | Ikeda et al. | |
| 5,959,058 A | 9/1999 | Tonelli et al. | |
| 11,261,394 B2* | 3/2022 | Kato | G11B 5/73911 |
| 2010/0233513 A1 | 9/2010 | Imai et al. | |
| 2010/0261039 A1 | 10/2010 | Itoh et al. | |
| 2012/0225217 A1 | 9/2012 | Itoh et al. | |
| 2013/0209837 A1 | 8/2013 | Sagata et al. | |
| 2016/0203839 A1 | 7/2016 | Shimizu | |
| 2017/0260472 A1 | 9/2017 | Sagata et al. | |
| 2017/0331155 A1* | 11/2017 | Yang | H01M 4/136 |
| 2018/0127543 A1 | 5/2018 | Watanabe et al. | |
| 2021/0062102 A1 | 3/2021 | Kato et al. | |

FOREIGN PATENT DOCUMENTS

| | | |
|---|---|---|
| JP | 57-176973 A | 10/1982 |
| JP | 03-7798 A | 1/1991 |
| JP | 05-12655 A | 1/1993 |
| JP | 08-259882 A | 10/1996 |
| JP | 10-106822 A | 4/1998 |
| JP | 11-60720 A | 3/1999 |
| JP | 2009-266360 A | 11/2009 |
| JP | 2010-143855 A | 7/2010 |
| JP | 2010-282707 A | 12/2010 |
| JP | 4632144 B2 | 2/2011 |
| JP | 2012-9090 A | 1/2012 |
| JP | 2013-163667 A | 8/2013 |
| JP | 5465454 B2 | 4/2014 |
| JP | 5909837 B2 | 4/2016 |
| JP | 2018-076404 A | 5/2018 |
| WO | 2009/035075 A1 | 3/2009 |
| WO | 2016/084781 A1 | 6/2016 |
| WO | 2017/145995 A1 | 8/2017 |

OTHER PUBLICATIONS

International Search Report of PCT/JP2018/028455 dated Oct. 2, 2018 [PCT/ISA/210].
International Search Report for PCT/JP2018/031161 dated, Nov. 27, 2018 (PCT/ISA/210).
Office Action dated Jul. 23, 2021 in U.S. Appl. No. 16/644,586.
Notice of Allowance dated Dec. 2, 2021 in U.S. Appl. No. 16/644,586.
Notice of Allowance dated Nov. 9, 2021 in U.S. Appl. No. 16/644,586.

* cited by examiner

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2018/028455, filed Jul. 30, 2018, claiming priority to Japanese Patent Application No. 2017-158650, filed Aug. 21, 2017, the contents of all of which are incorporated herein by reference in their entirety.

BACKGROUND OF THE INVENTION

Field of the Invention

The present invention relates to a fluorine-containing ether compound suitable for use as a lubricant for magnetic recording media, a lubricant for magnetic recording media containing the same, and a magnetic recording medium.

Description of Related Art

In recent years, as information processing capacity increases, various information recording technologies have been developed. In particular, a magnetic recording medium suitable for high recording density has been developed.

Conventionally, in a magnetic recording medium, a protective layer and a lubricant layer are provided on the magnetic recording layer formed on the substrate in order to ensure the durability and reliability of the magnetic recording medium. In particular, various characteristics such as long-term stability, chemical substance resistance (preventing contamination such as siloxane) and wear resistance are required for the lubricant layer used for the outermost surface.

Conventionally, as a lubricant for a magnetic recording medium, a perfluoropolyether lubricant having a polar group such as a hydroxy group at the terminal of a fluorine polymer having a repeating structure containing $CF_2$ has been often used. (For example, see Patent Documents 1 to 3)

For example, Patent Document 1 discloses a compound in which a substituent, having a plurality of hydroxy groups and having a shortest distance of 3 atoms or more between the hydroxy groups, is provided at both terminal portions. Patent Document 2 discloses a fluoropolyether compound having an aromatic group at one terminal and a hydroxy group at the other terminal. Patent Document 3 discloses a compound having a perfluoropolyether main chain, having an aromatic group and a hydroxy group at the terminals of the molecule, wherein the aromatic group and the hydroxy group are bonded to different carbon atoms.

PATENT DOCUMENT

[Patent Document 1] Japanese Patent No. 4632144
[Patent Document 2] Japanese Patent No. 59909375909837
[Patent Document 3] Japanese Patent No. 5465454

SUMMARY OF THE INVENTION

In recent years, as the information recording density of a magnetic disk rapidly increases, it has been required to reduce the magnetic spacing between the magnetic head and the recording layer of the magnetic disk. For this reason, it is necessary to further reduce the thickness of the lubricant layer existing between the magnetic head and the recording layer of the magnetic disk. The lubricant used for the lubricant layer has a great influence on the reliability of the magnetic disk. Therefore, it is necessary to reduce the thickness of the lubricant layer while ensuring reliability such as wear resistance which is essential for the magnetic disk.

In addition, the environmental resistance requirements for magnetic disks have become very stringent due to diversification of applications of magnetic disks. For this reason, it is required to improve the wear resistance and chemical substance resistance of the lubricant layer, which greatly affects the reliability of the magnetic disk, over those of the prior art.

However, generally, when the thickness of the lubricant layer is reduced, the coverage is reduced, and the chemical substance resistance and the wear resistance tend to deteriorate.

Conventionally, the presence of polar groups such as hydroxy groups in the molecules of the lubricant provides good adhesion properties of the lubricant to the protective layer. Therefore, a perfluoropolyether lubricant having a plurality of hydroxy groups in the molecule has been preferably used.

However, even if the lubricant molecules have a plurality of polar groups such as hydroxy groups, the adhesion (adhesive strength) of the lubricant to the protective layer cannot be sufficiently enhanced unless the polar groups are effectively involved in bonding with the active point on the protective layer when the lubricant molecules are deposited on the protective layer.

A lubricant having low (inadequate) adhesion to a protective layer is bulky, and it is difficult to obtain a lubricant layer having a uniform film thickness with good coverage. For this reason, unless the film thickness is made relatively thick, the wear resistance and chemical substance resistance deteriorate, resulting in a problem that magnetic spacing cannot be reduced.

Also, if there are many polar groups in the lubricant molecules that are not involved in the bonding with the active points on the protective film, contaminations are attracted or pickup, in which the lubricant adheres to the magnetic head as foreign substance (smear), tends to occur.

The present invention has been made in view of the above circumstances, and an object of the present invention is to provide a fluorine-containing ether compound capable of forming a lubricant layer having excellent chemical substance resistance and wear resistance even when the thickness is small, which can be suitably used as a material for a lubricant for a magnetic recording medium.

Another object of the present invention is to provide a lubricant for magnetic recording medium containing the fluorine-containing ether compound of the present invention.

Another object of the present invention is to provide a magnetic recording medium having a lubricant layer containing the fluorine-containing ether compound of the present invention.

Means for Solving the Problems

The present inventors have conducted extensive research to solve the above problems.

As a result, the present inventors have found that a fluorine-containing ether compound can be used, in which a divalent linkage group having a polar group is linked to both terminals of a perfluoropolyether chain, and a terminal group, which is an organic group having 1 to 8 carbon atoms and at least one of hydrogen atoms of the organic group is substituted with a cyano group, is bonded to at least one of the linkage groups.

That is, the present invention relates to the following matters.

[1] A fluorine-containing ether compound represented by the following formula (1), $$R^1-R^2-CH_2-R^3-CH_2-R^4-R^5 \qquad (1)$$

wherein in the formula (1), $R^3$ is a perfluoropolyether chain; $R^2$ and $R^4$ are divalent linkage groups having a polar group and may be the same or different; $R^1$ and $R^5$ are terminal groups bonded to $R^2$ or $R^4$ and may be the same or different; and at least one of $R^1$ and $R^5$ is an organic group having 1 to 8 carbon atoms wherein one or more hydrogen atoms of the organic group is substituted with a cyano group.

[2] The fluorine-containing ether compound according to [1], wherein the organic group is a phenyl group or an alkyl group having 1 to 5 carbon atoms.

[3] The fluorine-containing ether compound according to [1] or [2], wherein the polar group is a hydroxy group.

[4] The fluorine-containing ether compound according to any one of [1] to [3], wherein $R^2$ and $R^4$ in the formula (1) are represented by the following formula (2-1), $$-(X-CH_2CH(OH)CH_2)_a-X- \qquad (2-1)$$

wherein in the formula (2-1), a represents an integer of 1 to 3, X represents an oxygen atom or $CH_2$, and two X may be the same or different.

[5] The fluorine-containing ether compound according to [4], wherein a in the formula (2-1) is 1 or 2, and each X is an oxygen atom.

[6] The fluorine-containing ether compound according to any one of [1] to [5], wherein $R^3$ in the formula (1) is any one of the following formulas (3) to (5), $$-CF_2O-(CF_2CF_2O)_c-(CF_2O)_d-CF_2- \qquad (3)$$

wherein c and d in the formula (3) represent an average degree of polymerization and each represents 0 to 20, and c or d is 0.1 or more;

$$-CF(CF_3)-(OCF(CF_3)CF_2)_e-OCF(CF_3)- \qquad (4)$$

wherein in formula (4), e represents an average degree of polymerization and represents 0.1 to 20; and $$-CF_2CF_2-(OCF_2CF_2CF_2)_f-OCF_2CF_2- \qquad (5)$$

wherein in the formula (5), f represents an average degree of polymerization and represents 0.1 to 20.

[7] The fluorine-containing ether compound according to any one of [1] to [6], wherein $R^1$ and $R^5$ in the formula (1) are the same, and $R^2$ and $R^4$ are the same.

[8] The fluorine-containing ether compound according to [7], wherein $R^1$ and $R^5$ in the formula (1) are alkyl groups having 1 to 5 carbon atoms wherein the alkyl groups are substituted with at least one cyano group.

[9] The fluorine-containing ether compound according to any one of [1] to [6], wherein $R^1$ and $R^5$ in the formula (1) are different, and one of $R^1$ and R is a phenyl group substituted with at least one cyano group or an alkyl group having 1 to 5 carbon atoms substituted with at least one cyano group, and the other of $R^1$ and $R^5$ is an organic group having at least one selected from the group consisting of an aromatic ring, a heterocyclic ring, an alkenyl group, an alkynyl group and a hydroxy group.

[10] The fluorine-containing ether compound according to any one of [1] to [9], wherein the number average molecular weight is in the range of 500 to 10,000.

[11] A lubricant for magnetic recording media, comprising the fluorine-containing ether compound according to any one of [1] to [10].

[12] A magnetic recording medium in which at least a magnetic layer, a protective layer, and a lubricant layer are sequentially provided on a substrate, wherein the lubricant layer contains the fluorine-containing ether compound according to any one of [1] to [10].

[13] The magnetic recording medium according to [12], wherein an average film thickness of the lubricant layer is 0.5 nm to 2 nm.

The fluorine-containing ether compound of the present invention is suitable to be used as a material for a lubricant for magnetic recording media. Since the lubricant for magnetic recording media of the present invention contains the fluorine-containing ether compound of the present invention, a lubricant layer having excellent chemical substance resistance and wear resistance can be formed even if the thickness is small.

Since the magnetic recording medium of the present invention has a lubricant layer having excellent chemical substance resistance and wear resistance, it is excellent in reliability and durability.

DETAILED DESCRIPTION OF THE INVENTION

Figure 1:
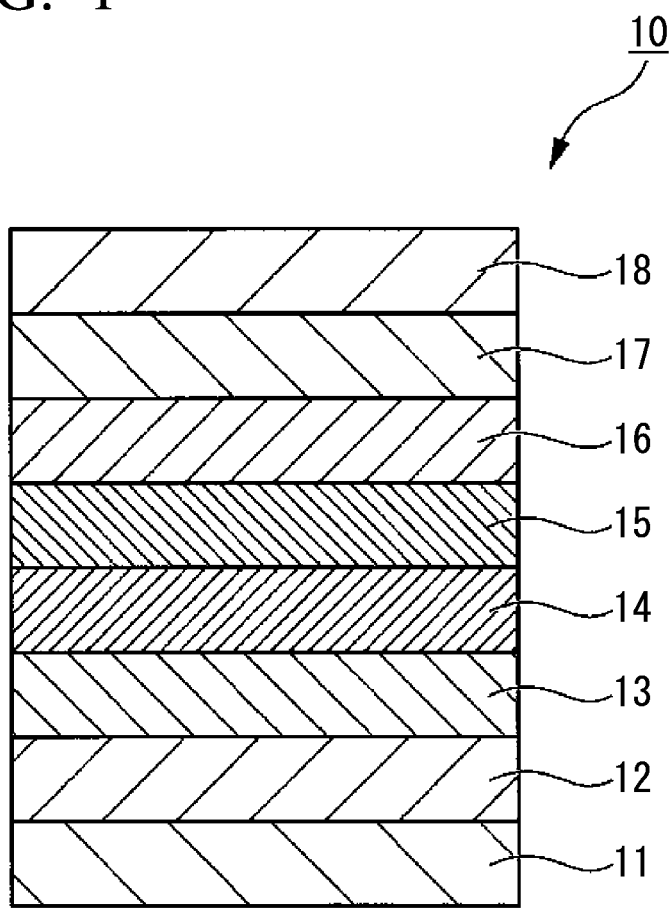
FIG. 1 is a schematic cross-sectional view showing an embodiment of a magnetic recording medium of the present invention.

Hereinafter, the fluorine-containing ether compound, the lubricant for magnetic recording media (hereinafter sometimes referred to as "lubricant") and the magnetic recording medium of the present invention will be described in detail. This invention is not limited only to embodiments shown below.

[Fluorine-Containing Ether Compound]

The fluorine-containing ether compound of this embodiment is represented by the following formula (1).

$$R^1-R^2-CH_2-R^3-CH_2-R^4-R^5 \qquad (1)$$

In the formula (1), $R^3$ is a perfluoropolyether chain; $R^2$ and $R^4$ are divalent linkage groups having a polar group and may be the same or different; $R^1$ and $R^5$ are terminal groups bonded to $R^2$ or $R^4$ and may be the same or different; and at least one of $R^1$ and $R^5$ is an organic group having 1 to 8 carbon atoms wherein one or more hydrogen atoms of the organic group is substituted with a cyano group.

In the fluorine-containing ether compound of the present embodiment represented by the above formula (1), $R^1$ and $R^5$ are terminal groups bonded to $R^2$ and $R^4$ respectively and may be the same or different. The organic group forming the terminal group may contain an oxygen atom, a sulfur atom, a nitrogen atom, or the like.

At least one of R and $R^5$ is a group in which one or more hydrogen atoms of an organic group having 1 to 8 carbon atoms are substituted with a cyano group (—CN) (hereinafter referred to as "a cyano group-substituted organic group").

In the fluorinated ether compound of this embodiment, the cyano group (—CN) in $R^1$ and the polar group in $R^2$, and/or the cyano group in $R^5$ and the polar group in $R^4$ show good interaction with the protective layer in the lubricant layer containing the fluorinated ether compound.

In the cyano group-substituted organic group, the carbon forming the cyano group is difficult to rotate freely because it has an SP hybrid orbital. Therefore, the intramolecular interaction (affinity) of the cyano group in the fluorine-containing ether compound is relatively low. Therefore, it is presumed that each of the cyano group-substituted organic group of at least one of $R^1$ and $R^5$ and the polar group (for example, a hydroxy group) of $R^2$ or $R^4$ independently interacts with a large number of functional groups on the surface of the protective layer, and as a result, affinity with the protective layer increases.

In contrast, for example, regarding a conventional fluorine-containing ether compound having an organic group substituted with a hydroxy group instead of the cyano group-substituted organic group in the present embodiment, affinity with the protective layer is weak, as compared with the fluorine-containing ether compound of the present embodiment. It is presumed that this is because the degree of freedom of rotation of the hydroxy group is higher than that of the cyano group, and the organic group substituted with the hydroxy group and the polar group (for example, hydroxy group) of $R^2$ or $R^4$ are likely to interact with each other.

In the fluorine-containing ether compound of the present embodiment, the type of the cyano group-substituted organic group can be appropriately selected according to the performance required for the lubricant containing the fluorine-containing ether compound.

The number of cyano groups (—CN) in the cyano group-substituted organic group at at least one of $R^1$ and $R^5$ is not particularly limited, and may be one or two or more. When the number of cyano groups (—CN) is 3 or more, the polarity of the fluorine-containing ether compound becomes too high, and there is a possibility that pickup, in which the fluorine-containing ether compound adheres to the magnetic head as foreign substance (smear), may occur. It is preferable that the number of the cyano groups (—CN) is 2 or less, because pickup can be prevented.

The number of carbon atoms of the organic group in the cyano group-substituted organic group is 1 to 8. When the number of carbon atoms is 1 to 8, the affinity between the lubricant layer containing the fluorinated ether compound and the protective layer is further improved.

As the cyano group-substituted organic group, the organic group having 1 to 8 carbon atoms is preferably a phenyl group or an alkyl group having 1 to 5 carbon atoms. When it is a phenyl group, excellent wear resistance is obtained. When it is an alkyl group having 1 to 5 carbon atoms, steric hindrance is suppressed, and an effect of large affinity between the protective layer and the cyano group can thus be obtained.

Examples of the cyano group-substituted organic groups include organic groups substituted with cyano groups represented by any one of the formulas (6-1) to (12). Among these organic groups substituted with the cyano groups, from the viewpoint of good affinity with the protective layer of the magnetic recording medium, cyano group-substituted organic groups represented by the formulas (6-1) to (6-4), (7), (10), and (11) are preferable. From the viewpoint of achieving both excellent wear resistance and good affinity with the protective layer, cyano group-substituted organic groups represented by the formulas (9-1) to (9-5) are preferable. The dotted line in any one of the formulas (6-1) to (12) is a bond bonded to $R^2$ or $R^4$.

[Chemical Formula1]

(6-1)

(6-2)

(6-3)

(6-4)

(7)

(8)

(9-1)

(9-2)

(9-3)

(9-4)

(9-5)

(10)

(11)

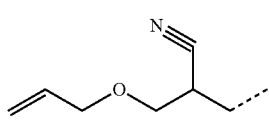

(12)

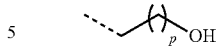

(13)

When only one terminal group of $R^1$ and $R^5$ (for example, $R^5$) is a cyano group-substituted organic group, the other terminal group (for example, R) that is not a cyano group-substituted organic group is not particularly limited. The other terminal group is preferably an organic group having at least one double bond or triple bond, and examples thereof include a group containing an aromatic ring, a group containing a heterocyclic ring, a group containing an alkenyl group, and a group containing an alkynyl group. Alternatively, the other terminal group is preferably an alkyl group having 1 to 8 carbon atoms and the alkyl group may have a substituent.

Specifically, the other terminal group may be a phenyl group, a methoxyphenyl group, a fluorinated phenyl group, a naphthyl group, a phenethyl group, a methoxyphenethyl group, a fluorinated phenethyl group, a benzyl group, a methoxybenzyl group, a naphthylmethyl group, a methoxynaphthyl group, a pyrrolyl group, a pyrazolyl group, a methylpyrazolylmethyl group, an imidazolyl group, a furyl group, a furfuryl group, an oxazolyl group, an isoxazolyl group, a thienyl group, a thienylethyl group, a thiazolyl group, a methylthiazolylethyl group, an isothiazolyl group, a pyridyl group, a pyrimidinyl group, a pyridazinyl group, a pyrazinyl group, an indolinyl group, a benzofuranyl group, a benzothienyl group, a benzoimidazolyl group, a benzoxazolyl group, a benzothiazolyl group, a benzopyrazolyl group, a benzoisoxazolyl group, a benzoisothiazolyl group, a quinolyl group, an isoquinolyl group, a quinazolinyl group, a quinoxalinyl group, a phthalazinyl group, a cinnolinyl group, a vinyl group, an allyl group, a butenyl group, a propynyl group, a propargyl group, a butynyl group, a methylbutynyl group, a pentynyl group, a methylpentynyl group, a hexynyl group, a methyl group, an ethyl group, a propyl group, a butyl group, a pentyl group, a hexyl group, an octyl, a trifluoromethyl group, a perfluoroethyl group, a perfluoropropyl group, a perfluorobutyl group, a perfluoropentyl group, a perfluorohexyl group, an octafluoropentyl group, or a tridecafluorooctyl group.

Among the above groups, it is preferable that the other terminal group is a phenyl group, a methoxyphenyl group, a thienylethyl group, a butenyl group, an allyl group, a propargyl group, a phenethyl group, a methoxyphenethyl group, or a fluorinated phenethyl group. It is more preferable that the other terminal group is a phenyl group, a thienylethyl group, or an allyl group. In this case, the obtained fluorine-containing ether compound can form a lubricant layer having better wear resistance.

The other terminal group may have a substituent such as an alkyl group, an alkoxy group, a hydroxy group, a mercapto group, a carboxy group, a carbonyl group, or an amino group.

When only one terminal group of $R^1$ and $R^5$ (for example, $R^5$) is a cyano group-substituted organic group, it is preferable that the other terminal group (for example, $R^1$) that is not a cyano group-substituted organic group is an organic group having at least one polar group. For example, the terminal group having a hydroxy group represented by the formula (13) may be used.

[Chemical Formula 2]

(13)

In the formula (13), p represents an integer of 0 to 5.

When the other terminal group is a terminal group having one hydroxy group represented by the formula (13), the affinity between the lubricant layer containing the fluorine-containing ether compound and the protective layer is further improved, which is preferable.

In the formula (13), p represents an integer of 0 to 5, and preferably p represents an integer of 0 to 2. It is preferable that p is 5 or less because the surface free energy of the whole molecule does not become too high due to the low proportion of fluorine atoms in the molecule.

That is, when $R^1$ and $R^5$ in the formula (1) are different and only one terminal group of $R^1$ and $R^5$ is a cyano group-substituted organic group, it is more preferable that one of $R^1$ and $R^5$ is a phenyl group substituted with at least one or more cyano groups or an alkyl group having 1 to 5 carbon atoms substituted with one or more cyano groups; and the other of $R^1$ and $R^5$ is an organic group having at least one selected from the group of an aromatic ring, a heterocyclic ring, an alkenyl group, an alkynyl group or a hydroxy group.

$R^2$ and $R^4$ in the formula (1) are divalent linkage groups having a polar group. $R^2$ and $R^4$ may be the same or different. Since $R^2$ and $R^4$ in the formula (1) have a polar group, when the lubricant layer is formed on the protective layer using the lubricant containing the fluorine-containing ether compound of this embodiment, a suitable interaction between the lubricant layer and the protective layer occurs. The divalent linkage group having a polar group can be appropriately selected according to the performance required for the lubricant containing the fluorine-containing ether compound.

Examples of the polar group of the divalent linkage group having a polar group include a hydroxy group (—OH), an amino group (—NH$_2$), a carboxy group (—COOH), a formyl group (—COH), a carbonyl group (—CO—), a sulfonic acid group (—SO$_3$H) and the like. Of these, the polar group is particularly preferably a hydroxy group. The hydroxy group interacts strongly with a protective layer, particularly a protective layer formed of a carbon-based material. Therefore, when the polar group is a hydroxy group, the lubricant layer containing the fluorine-containing ether compound has high adhesion to the protective layer.

$R^2$ and $R^4$ in the formula (1) are preferably the following formula (2-1).

—(X—CH$_2$CH(OH)CH$_2$)$_a$—X—  (2-1)

In the formula (2-1), a is an integer of 1 to 3, and X represents O (oxygen atom) or CH$_2$.)

When in the formula (2-1), a is 1 or more, the interaction between the polar groups of $R^2$ and $R^4$ and the protective layer becomes even stronger. As a result, by using the fluorine-containing ether compound, it is possible to obtain a lubricant layer having higher adhesion to the protective layer. Further, when the above a is 3 or less, it is possible to prevent pickup, in which the fluorine-containing ether compound adheres to the magnetic head as a foreign substance (smear) due to high polarity of the fluorine-containing ether compound. In the formula (2-1), a is preferably 1 or 2.

The two X in the formula (2-1) may be the same or different.

Of the two X in formula (2-1), at least one is preferably an oxygen atom, and more preferably both are oxygen atoms.

When at least one of the two X in the formula (2-1) is an oxygen atom, the interaction between the polar group and the protective layer becomes stronger as compared to the case where the two X are both $CH_2$.

In the fluorine-containing ether compound represented by the formula (1), when $R^2$ and $R^4$ are represented by the above formula (2-1), a chain-bonded carbon atom (or chain-bonded carbon atom and an oxygen atom) is arranged between the cyano group of $R^1$ and/or $R^5$ and a carbon atom to which the polar group of $R^2$ and $R^4$ are bonded. Therefore, for example, as compared with the case where the cyano group of R and/or $R^5$ and the polar group of $R^2$ and $R^4$ are bonded to the same carbon (—C (polar group) —CN), the interaction between the cyano group and the polar group is weak. On the other hand, the interaction between both the cyano group and the polar group and a large number of functional groups present on the surface of the protective layer is relatively strong compared to the case where the cyano group and the polar group are bonded to the same carbon. As a result, the affinity between the lubricant layer and the protective layer increases when the lubricant layer is formed on the protective layer using the lubricant containing the fluorine-containing ether compound.

Therefore, when $R^2$ and $R^4$ are represented by the above formula (2-1), the lubricant layer formed using the lubricant containing the fluorine-containing ether compound has better chemical resistance and wear resistance. From the viewpoint of the affinity between the lubricant layer and the protective layer, the total number of chain-bonded carbon atoms and oxygen atoms present between the carbon to which a polar group is bonded in $R^2$ and/or $R^4$, which is bonded to a cyano group-substituted organic group of $R^1$ and/or $R^5$, and the cyano group is preferably 2 to 4.

$R^3$ in the formula (1) is a perfluoropolyether chain (hereinafter sometimes abbreviated as "PFPE chain"). In the lubricant layer containing the fluorine-containing ether compound of this embodiment, the PFPE chain covers the surface of the protective layer and reduces the frictional force between the magnetic head and the protective layer. The PFPE chain can be appropriately selected according to the performance required for the lubricant containing the fluorine-containing ether compound.

Examples of the PFPE chain include a perfluoromethylene oxide polymer, a perfluoroethylene oxide polymer, a perfluoro-n-propylene oxide polymer, a perfluoroisopropylene oxide polymer, and a copolymer thereof.

Specifically, $R^3$ in the formula (1) is preferably any one of the following formulas (3) to (5). When $R^3$ is any one of the formulas (3) to (5), a fluorine-containing ether compound which may be used for a lubricant layer having good lubricity can be obtained.

In addition, $(CF_2CF_2O)$ and $(CF_2O)$ which are repeating units in the formula (3) may be bonded in a block manner, or a part or all of them may be bonded at random.

$$—CF_2O—(CF_2CF_2O)_c—(CF_2O)_d—CF_2— \quad (3)$$

In the formula (3), c and d represent the average degree of polymerization and each represents 0 to 20, and c or d is 0.1 or more.

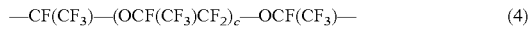  (4)

In the formula (4), e represents the average degree of polymerization and represents 0.1 to 20.

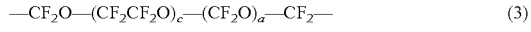  (5)

In the formula (5), f represents the average degree of polymerization and represents 0.1 to 20.

In the formulas (4) to (5), e and f are each 0.1 to 20 (or in the formula (3), c and d are each 0 to 20 and c or d is 0.1 or more). Thus, a fluorine-containing ether compound which may be used to produce a lubricant layer having good lubricity can be obtained. However, when c, d, e, and f exceed 20, the viscosity of the fluorine-containing ether compound increases, and it may be difficult to apply a lubricant containing the compound. Therefore, c, d, e, and f are preferably 20 or less.

In the fluorine-containing ether compound represented by the formula (1), $R^1$ and $R^5$ may be the same or different. $R^1$ and $R^5$ are preferably the same in view of ease of production.

In the fluorine-containing ether compound represented by the formula (1), $R^2$ and $R^4$ may be the same or different. $R^2$ and $R^4$ are preferably the same in view of ease of production.

Therefore, it is preferable that R and $R^5$ of the fluorine-containing ether compound represented by the formula (1) are the same and that $R^2$ and $R^4$ of the fluorine-containing ether compound represented by the formula (1) are the same in view of ease of production. When $R^1$ and $R^5$ are the same, and $R^2$ and $R^4$ are the same, it is more preferable that R and $R^5$ are alkyl groups having 1 to 5 carbon atoms, which is substituted with at least one cyano group in view of improving adhesion between the lubricant layer and the protective layer.

Specifically, the fluorine-containing ether compound represented by the formula (1) is preferably any one of compounds represented by the following formulas (A) to (R) and (V) to (AR). Note that the repetition numbers m and n in the formulas (A) to (R) and (V) to (AR) are values indicating average values, and are not necessarily integers.

In the compounds represented by formulas (A) to (G), $R^1$ and $R^5$ are each one of cyano group-substituted organic groups represented by formulas (6) to (12); $R^2$ and $R^4$ are each represented by the formula (2-1) in which a is 1 and X is O (oxygen atom); R and $R^5$ are the same and $R^2$ and $R^4$ are the same; and $R^3$ is represented by the formula (3).

In the compounds represented by formulas (H) to (J) and (L) to (O), $R^1$ and $R^5$ are different, $R^5$ is one of cyano group-substituted organic groups represented by formulas (6) to (10), $R^1$ is one of a phenyl group, a thienylethyl group, and an allyl group; $R^2$ and $R^4$ are the same, and $R^2$ and $R^4$ are each represented by the formula (2-1) in which a is 1 and X is O (oxygen atom); and $R^3$ is represented by the formula (3).

In the compound represented by the formula (K), $R^1$ and $R^5$ are different; $R^5$ is a cyano group-substituted organic group represented by the formula (6), $R^1$ is an allyl group; $R^2$ and $R^4$ are different, $R^2$ is represented by the formula (2-1) in which a is 2 and X is O, and $R^4$ is represented by the formula (2-1) in which a is 1 and X is O; and $R^3$ is formula (3).

In the compound represented by the formula (P), $R^1$ and $R^5$ are different, $R^5$ is a cyano group-substituted organic group represented by the formula (6), and $R^1$ is a cyano group-substituted organic group represented by the formula (12); $R^2$ and $R^4$ are the same, $R^2$ is represented by the formula (2-1) in which a is 1 and X is O; and $R^3$ is formula (3).

In the compound represented by the formula (Q), $R^1$ and $R^5$ are different, $R^5$ is represented by the formula (13) in which p is 1, and R is a cyano group-substituted organic group represented by the formula (12); $R^2$ and $R^4$ are the same, $R^2$ is represented by the formula (2-1) in which a is 1 and X is O; and $R^3$ is formula (3).

In the compound represented by the formula (R), $R^1$ and $R^5$ are different, $R^5$ is a cyano group-substituted organic group represented by the formula (6), and $R^1$ is an allyl group; $R^2$ and $R^4$ are different, $R^2$ is represented by the formula (2-1) in which a is 2 and X is O, and $R^4$ is represented by the formula (2-1), in which a is 1 and X is O; and $R^3$ is represented by the formula (5).

In the compound represented by the formula (V), $R^1$ and $R^5$ are each a cyano group-substituted organic group represented by the formula (6-2); and $R^2$ and $R^4$ are each represented by the formula (2-1) in which a is 1 and X is O (oxygen atom); $R^1$ and $R^5$ are the same and $R^2$ and $R^4$ are the same; and $R^3$ is represented by the formula (3).

In the compound represented by the formula (W), $R^1$ and $R^5$ are different, $R^5$ is represented by the formula (13) in which p is 1, and $R^1$ is a cyano group-substituted organic group represented by the formula (6-2); $R^2$ and $R^4$ are the same, $R^2$ is represented by the formula (2-1) in which a is 1 and X is O; and $R^3$ is represented by the formula (3).

In the compound represented by the formula (Y), $R^1$ and $R^5$ are different, $R^5$ is an organic group represented by the formula (13) in which p is 1 and $R^1$ is a cyano group-substituted organic group represented by the formula (6-2); $R^2$ and $R^4$ are different, $R^2$ is represented by the formula (2-1) in which a is 1 and X is O, and $R^4$ is represented by the formula (2-1) in which a is 2 and X is O; and $R^3$ is represented by the formula (3).

In the compound represented by the formula (Z), $R^1$ and $R^5$ are different, $R^5$ is a cyano group-substituted organic group represented by (6-2), and $R^1$ is an allyl group; $R^2$ and $R^4$ are different, $R^2$ is represented by the formula (2-1) in which a is 2 and X is O, and $R^4$ is represented by the formula (2-1) in which a is 1 and X is O; and $R^3$ is represented by the formula (3).

In the compound represented by the formula (AA), $R^1$ and $R^5$ are different, $R^5$ is a cyano group-substituted organic group represented by the formula (6-2), and $R^1$ is a thienylethyl group; $R^2$ and $R^4$ are different, $R^2$ is represented by the formula (2-1) in which a is 2 and X is O, and $R^4$ is represented by the formula (2-1) in which a is 1 and X is O; and $R^3$ is formula (3).

In the compound represented by the formula (AB), $R^1$ and $R^5$ are each a cyano group-substituted organic group represented by the formula (6-2), and $R^2$ and $R^4$ are each represented by the formula (2-1) in which a is 2 and X is O (oxygen atom); and $R^3$ is represented by the formula (3).

In the compound represented by the formula (AC), $R^1$ and $R^5$ are different, $R^5$ is represented by the formula (13) in which p is 1 and $R^1$ is a cyano group-substituted organic group represented by the formula (6-2); $R^2$ and $R^4$ are different, $R^2$ is represented by the formula (2-1) in which a is 2 and X is O, and $R^4$ is represented by the formula (2-1) in which a is 1 and X is O; and $R^3$ is represented by the formula (3).

In the compound represented by the formula (AD), $R^1$ and $R^5$ are different, $R^5$ is an organic group represented by the formula (13) in which p is 1 and $R^1$ is a cyano group-substituted organic group represented by the formula (6-2); $R^2$ and $R^4$ are each represented by the formula (2-1) in which a is 2 and X is O (oxygen atom); and $R^3$ is represented by the formula (3).

In the compound represented by the formula (AE), $R^1$ and $R^5$ are different, $R^5$ is a cyano group-substituted organic group represented by (6-2), and $R^1$ is an allyl group; $R^2$ and $R^4$ are each represented by the formula (2-1) in which a is 2 and X is O (oxygen atom); and $R^3$ is represented by the formula (3).

In the compound represented by the formula (AF), $R^1$ and $R^5$ are different, $R^5$ is a cyano group-substituted organic group represented by the formula (6-2), and $R^1$ is a thienylethyl group; $R^2$ and $R^4$ are each represented by the formula (2-1) in which a is 2 and X is O (oxygen atom); and $R^3$ is formula (3).

In the compound represented by the formula (AG), $R^1$ and $R^5$ are different, $R^5$ is represented by the formula (13) in which p is 1, and $R^1$ is a cyano group-substituted organic group represented by the formula (6-2); $R^2$ and $R^4$ are different, $R^2$ is represented by the formula (2-1) in which a is 2 and X is O, $R^4$ is represented by the formula (2-1) in which a is 1 and two X are each O or $CH_2$; $R^3$ is represented by the formula (3).

In the compound represented by the formula (AH), $R^1$ and $R^5$ are different, $R^5$ is represented by the formula (13) in which p is 1 and $R^1$ is a cyano group-substituted organic group represented by the formula (9-1); $R^2$ and $R^4$ are each represented by the formula (2-1) in which a is 1 and X is O (oxygen atom); and $R^3$ is formula (3).

In the compound represented by the formula (AI), $R^1$ and $R^5$ are each a cyano group-substituted organic group represented by the formula (9-1); $R^2$ and $R^4$ are each represented by the formula (2-1) in which a is 2 and X is O (oxygen atom); and $R^3$ is represented by the formula (3).

In the compounds represented by the formula (AJ), the formula (AK), and the formula (AL), $R^1$ and $R^5$ are different, $R^5$ is represented by the formula (13) in which p is 1, and R is any one of cyano group-substituted organic groups represented by formulas (9-1) to (9-3); $R^2$ and $R^4$ are different, $R^2$ is represented by the formula (2-1) in which a is 2 and X is O, $R^4$ is represented by the formula (2-1) in which a is 1 and X is O; and $R^3$ is represented by the formula (3).

In the compound represented by the formula (AM), $R^1$ and $R^5$ are different, and $R^5$ is represented by the formula (13) in which p is 1 and $R^1$ is a cyano group-substituted organic group represented by the formula (9-2); $R^2$ and $R^4$ are each represented by the formula (2-1) in which a is 2 and X is O (oxygen atom); and $R^3$ is the formula (3).

In the compound represented by the formula (AN), $R^1$ and $R^5$ are different, $R^5$ is a cyano group-substituted organic group represented by the formula (6-2), and $R^1$ is a cyano group-substituted organic group represented by the formula (9-2); $R^2$ and $R^4$ are different, $R^2$ is the formula (2-1) in which a is 2 and X is O, and $R^4$ is the formula (2-1) in which a is 1 and X is O; and $R^3$ is the formula (3).

In the compound represented by the formula (AO), $R^1$ and $R^5$ are different, $R^5$ is a cyano group-substituted organic group represented by the formula (6-2), and $R^1$ is a cyano group-substituted organic group represented by the formula (9-2); $R^2$ and $R^4$ are each represented by the formula (2-1) in which a is 2 and X is O (oxygen atom); and $R^3$ is the formula (3).

In the compound represented by the formula (AP), $R^1$ and $R^5$ are each a cyano group-substituted organic group represented by the formula (6-2); $R^2$ and $R^4$ are different, $R^2$ is the formula (2-1) in which a is 1 and X is O and $R^4$ is the formula (2-1) in which a is 2 and X is O; and $R^3$ is the formula (3).

In the compound represented by the formula (AQ), $R^1$ and $R^5$ are different, $R^5$ is represented by the formula (13) in which p is 1 and $R^1$ is a cyano group-substituted organic group represented by the formula (9-2); $R^2$ and $R^4$ are each represented by the formula (2-1) in which a is 1 and X is O (oxygen atom); and $R^3$ is the formula (5).

In the compound represented by the formula (AR), $R^1$ and $R^5$ are different, $R^5$ is represented by the formula (13) in which p is 1 and $R^1$ is a cyano group-substituted organic group represented by the formula (9-2); $R^2$ and $R^4$ are each represented by the formula (2-1) in which a is 1 and X is O (oxygen atom); and $R^3$ is represented by the formula (3) in which d is 0.

[Chemical Formula 3]

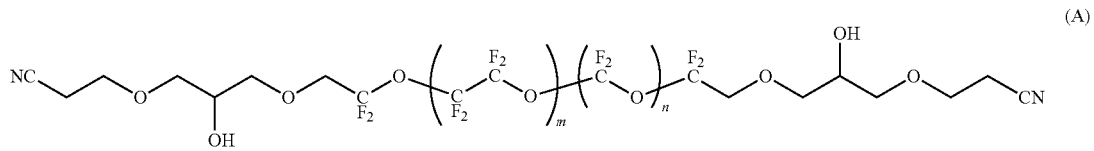
(A)

In the formula (A), m and n represent the average degree of polymerization and are each 0.1 to 20.

[Chemical Formula 4]

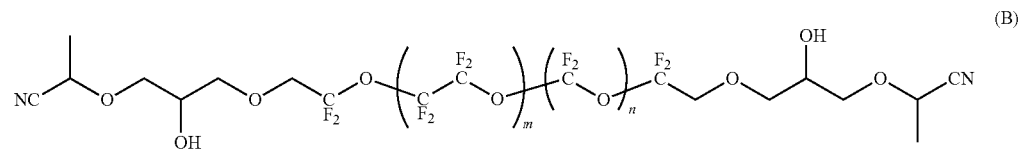
(B)

In the formula (B), m and n represent the average degree of polymerization and are each 0.1 to 20.

[Chemical Formula 5]

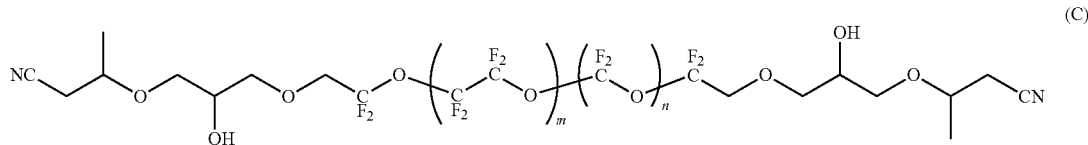
(C)

In the formula (C), m and n represent the average degree of polymerization and are each 0.1 to 20.

[Chemical Formula 6]

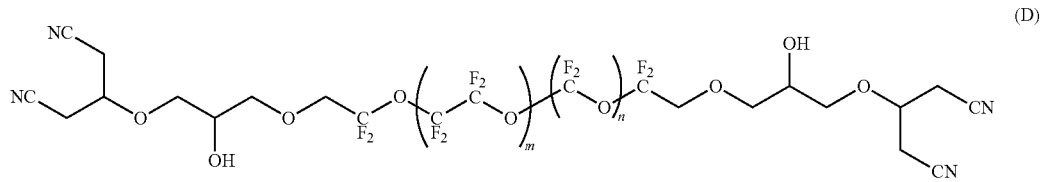
(D)

In the formula (D), m and n represent the average degree of polymerization and are each 0.1 to 20.

[Chemical Formula 7]

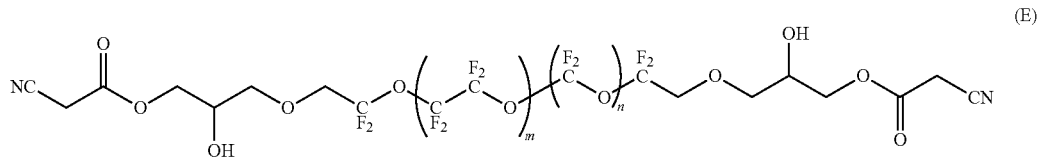
(E)

In the formula (E), m and n represent the average degree of polymerization and are each 0.1 to 20.

[Chemical Formula 8]

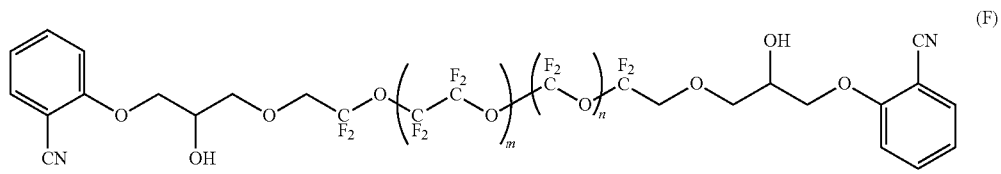
(F)

In the formula (F), m and n represent the average degree of polymerization and are each 0.1 to 20.

[Chemical Formula 9]

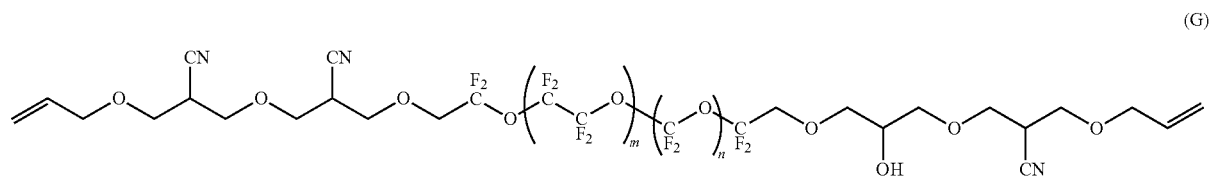
(G)

In the formula (G), m and n represent the average degree of polymerization and are each 0.1 to 20.

[Chemical Formula 10]

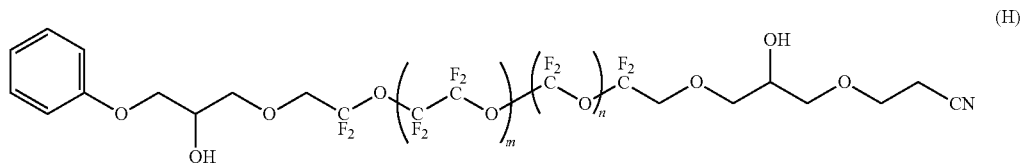
(H)

In the formula (H), m and n represent the average degree of polymerization and are each 0.1 to 20.

[Chemical Formula 11]

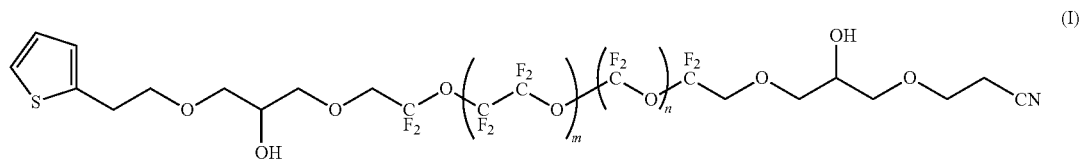
(I)

In the formula (I), m and n represent the average degree of polymerization and are each 0.1 to 20.

[General Formula 12]

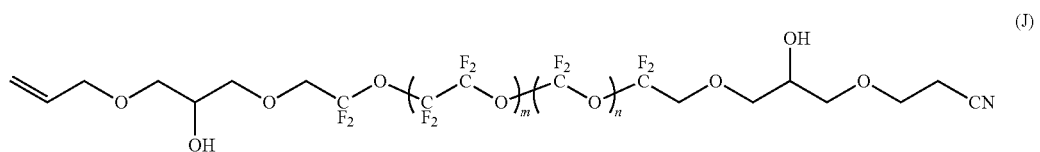
(J)

In the formula (J), m and n represent the average degree of polymerization and are each 0.1 to 20.

[Chemical Formula 13]

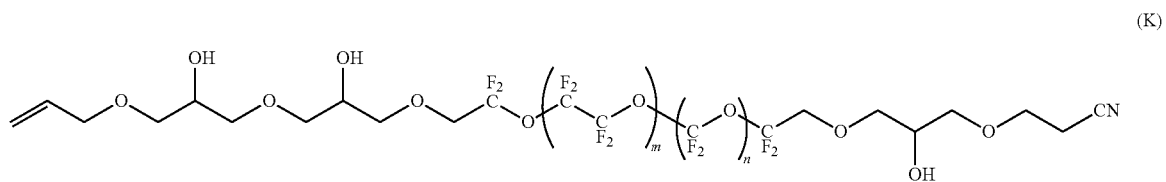
(K)

In the formula (K), m and n represent the average degree of polymerization and are each 0.1 to 20.

[Chemical Formula 14]

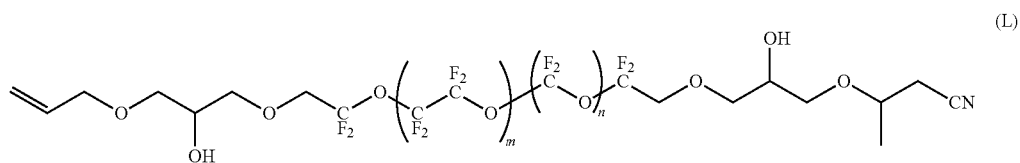
(L)

In the formula (L), m and n represent the average degree of polymerization and are each 0.1 to 20.

[Chemical Formula 15]

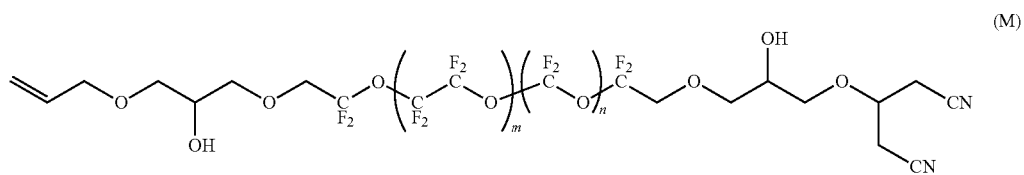
(M)

In the formula (M), m and n represent the average degree of polymerization and are each 0.1 to 20.

[Chemical Formula 16]

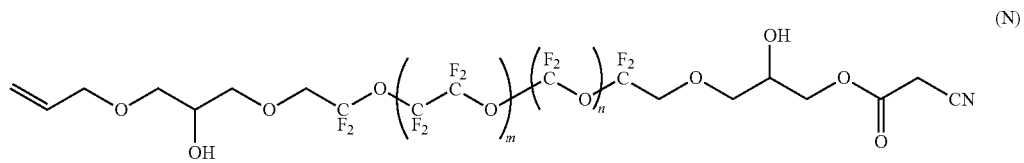
(N)

In the formula (N), m and n represent the average degree of polymerization and are each 0.1 to 20.

[Chemical Formula 17]

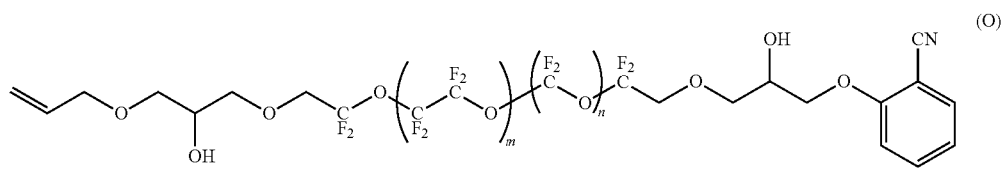
(O)

In the formula (O), m and n represent the average degree of polymerization and are each 0.1 to 20.

[Chemical Formula 18]

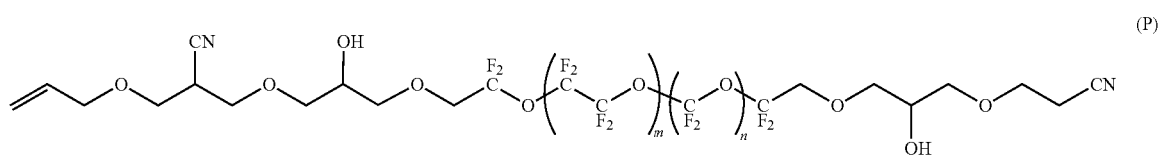
(P)

In the formula (P), m and n represent the average degree of polymerization and are each 0.1 to 20.

lp;1p

[Chemical Formula 19]

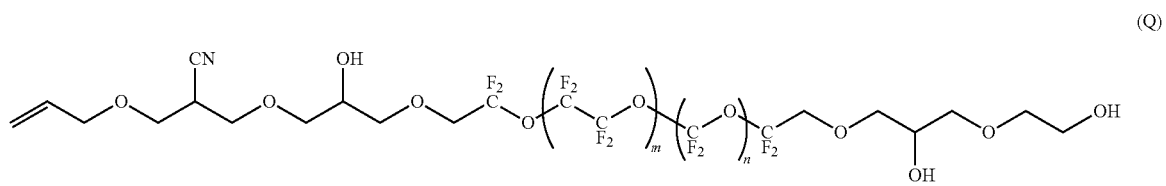
(Q)

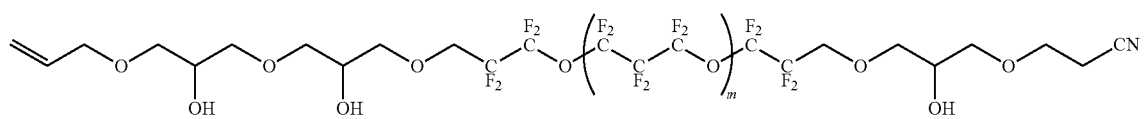
(R)

In the formula (Q), m and n represent the average degree of polymerization and are each 0.1 to 20.

In the formula (R), m represents the average degree of polymerization and is 0.1 to 20.

[Chemical Formula 20]

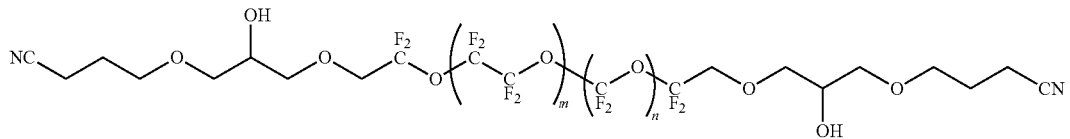

(V)

In the formula (V), m and n represent the average degree of polymerization and are each 0.1 to 20.

[Chemical Formula 21]

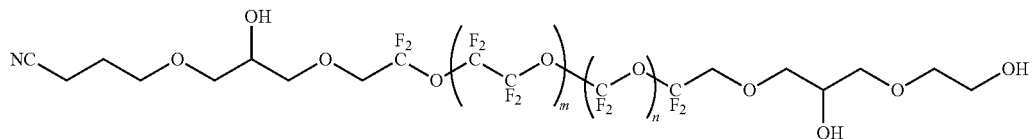

(W)

In the formula (W), m and n represent the average degree of polymerization and are each 0.1 to 20.

[Chemical Formula 22]

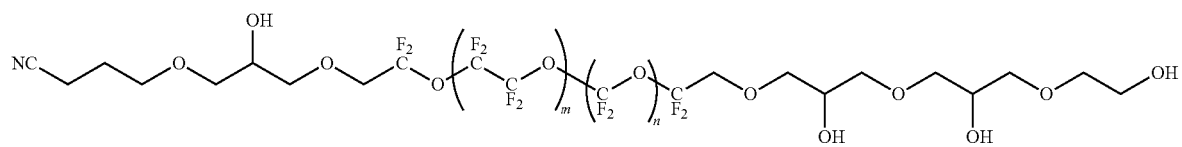

(Y)

In the formula (Y), m and n represent the average degree of polymerization and are each 0.1 to 20.

[Chemical Formula 23]

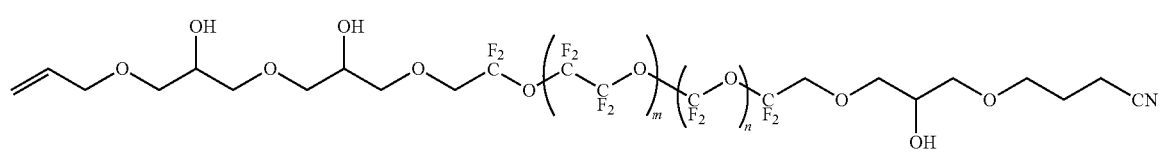

(Z)

In the formula (Z), m and n represent the average degree of polymerization and are each 0.1 to 20.

[Chemical Formula 24]

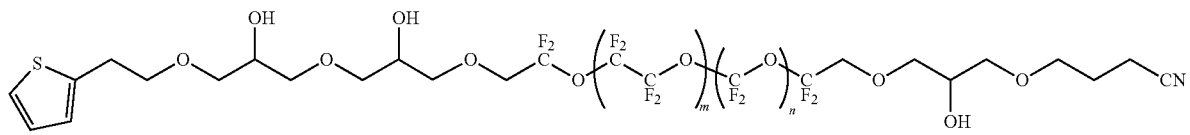
(AA)

In the formula (AA), m and n represent the average degree of polymerization and are each 0.1 to 20.

[Chemical Formula 25]

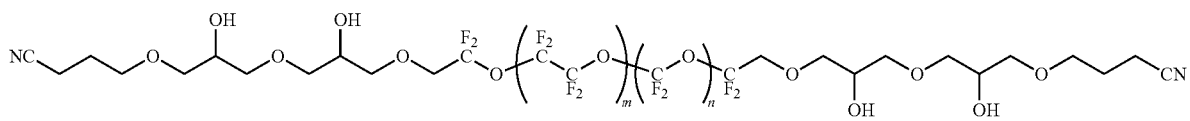
(AB)

In the formula (AB), m and n represent the average degree of polymerization and are each 0.1 to 20.

[Chemical Formula 26]

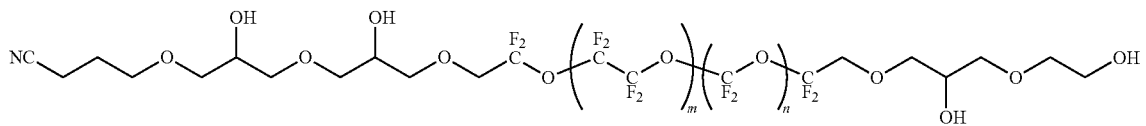
(AC)

In the formula (AC), m and n represent the average degree of polymerization and are each 0.1 to 20.

[Chemical Formula 27]

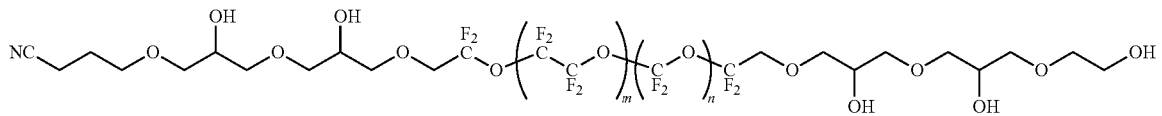
(AD)

In the formula (AD), m and n represent the average degree of polymerization and are each 0.1 to 20.

[Chemical Formula 28]

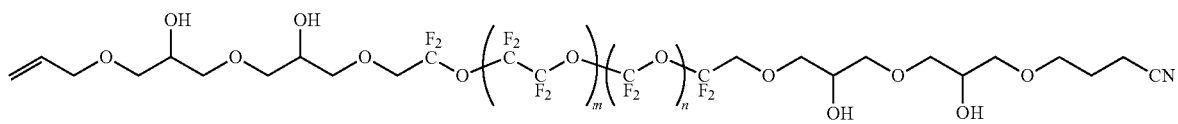
(AE)

In the formula (AE), m and n represent the average degree of polymerization and are each 0.1 to 20.

[Chemical Formula 29]

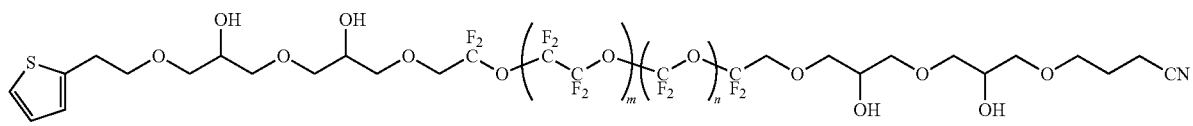
(AF)

In the formula (AF), m and n represent the average degree of polymerization and are each 0.1 to 20.

[Chemical Formula 30]

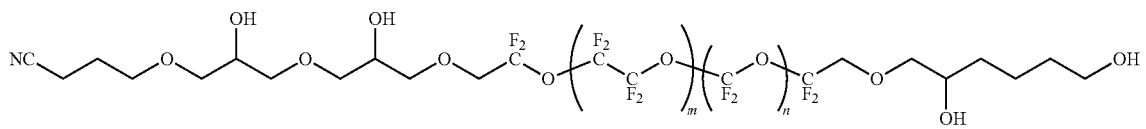
(AG)

In the formula (AG), m and n represent the average degree of polymerization and are each 0.1 to 20.

[Chemical Formula 31]

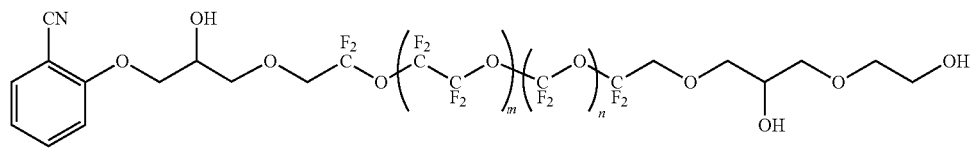
(AH)

In the formula (AH), m and n represent the average degree of polymerization and are each 0.1 to 20.

[Chemical Formula 32]

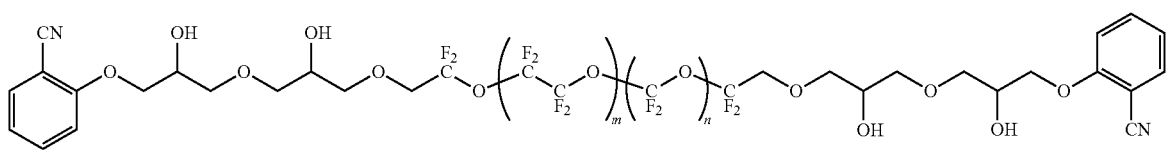
(AI)

In the formula (AI), m and n represent the average degree of polymerization and are each 0.1 to 20.

[Chemical Formula 33]

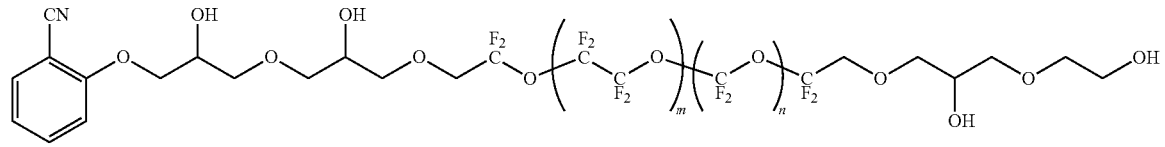
(AJ)

In the formula (AJ), m and n represent the average degree of polymerization and are each 0.1 to 20.

[Chemical Formula 34]

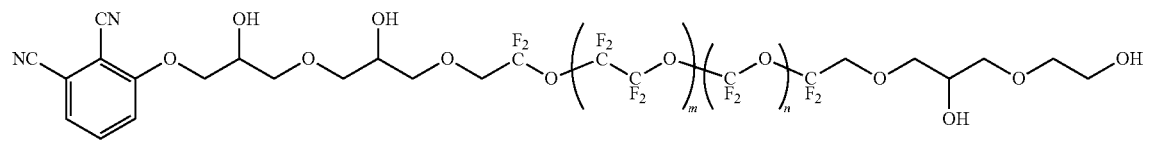
(AK)

In the formula (AK), m and n represent the average degree of polymerization and are each 0.1 to 20.

[Chemical Formula 35]

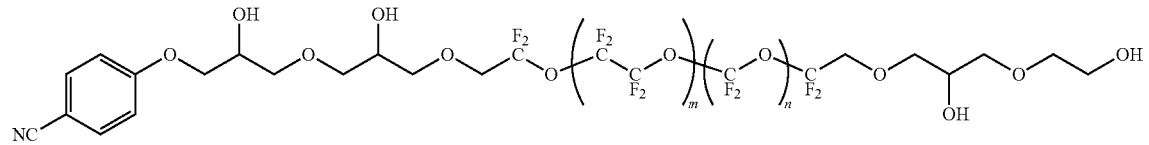
(AL)

In the formula (AL), m and n represent the average degree of polymerization and are each 0.1 to 20.

[Chemical Formula 36]

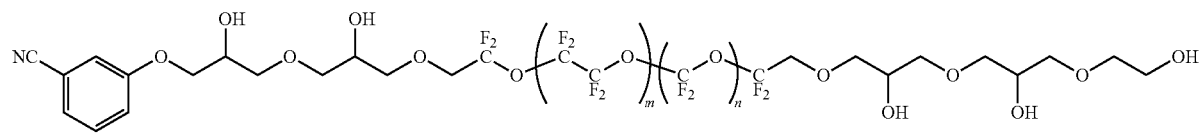
(AM)

In the formula (AM), m and n represent the average degree of polymerization and are each 0.1 to 20.

[Chemical Formula 37]

(AN)

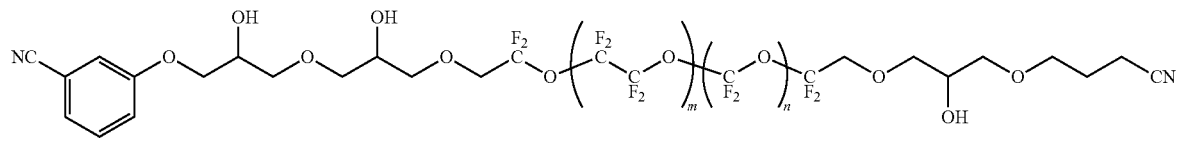

In the formula (AN), m and n represent the average degree of polymerization and are each 0.1 to 20.

[Chemical Formula 38]

(AO)

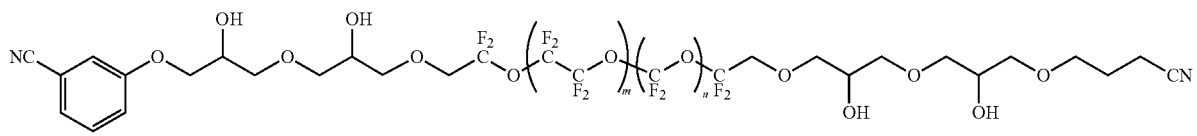

In the formula (AO), m and n represent the average degree of polymerization and are each 0.1 to 20.

[Chemical Formula 39]

(AP)

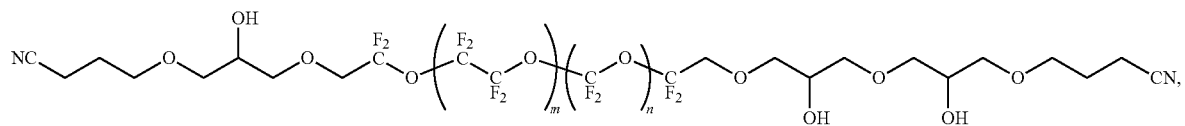

In the formula (AP), m and n represent the average degree of polymerization and are each 0.1 to 20.

[Chemical Formula 40]

(AQ)

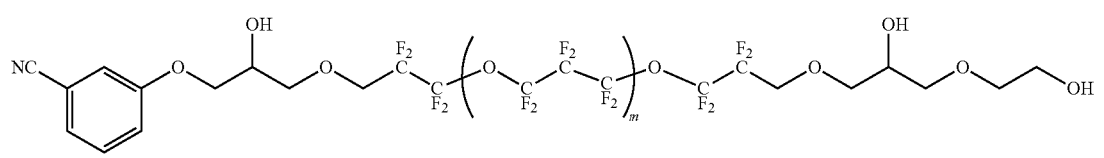

In the formula (AQ), m represents the average degree of polymerization and is 0.1 to 20.

[Chemical Formula 41]

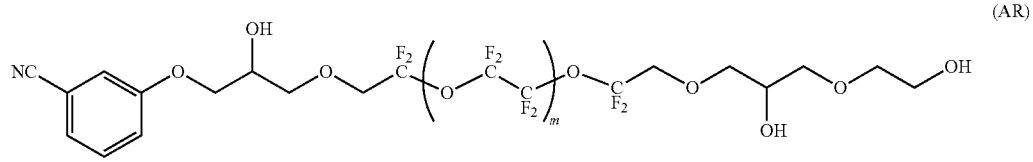

(AR)

In the formula (AR), m represents the average degree of polymerization and is 0.1 to 20.

The number average molecular weight (Mn) of the fluorine-containing ether compound represented by the formula (1) is preferably in the range of 500 to 10,000, particularly preferably 1,000 to 5,000. When the number average molecular weight is 500 or more, the lubricant layer containing the fluorine-containing ether compound of the present embodiment has excellent heat resistance. The number average molecular weight of the fluorinated ether compound is more preferably 1000 or more. Further, when the number average molecular weight is 10,000 or less, the viscosity of the fluorine-containing ether compound becomes appropriate, and a thin lubricant layer can be easily formed by applying a lubricant containing the fluorine-containing ether compound. The number average molecular weight of the fluorine-containing ether compound is preferably 5000 or less because the viscosity of the lubricant using the fluorine-containing ether compound becomes easy to handle.

The number average molecular weight (Mn) of the fluorine-containing ether compound is a value measured by $^1$H-NMR and $^{19}$F-NMR by using AVANCE III-400 manufactured by Bruker BioSpin. Specifically, the number of repeating units of the PFPE chain are calculated from the integral value measured by $^{19}$F-NMR, and then the number average molecular weight are calculated. In NMR (nuclear magnetic resonance) measurement, the sample is diluted in deuterated acetone solvent (hexafluorobenzene is added as a reference substance) and is used for measurement. The standard of $^{19}$F-NMR chemical shift was set to −164.7 ppm for the peak of hexafluorobenzene, and the standard of $^1$H-NMR chemical shift was set to 2.05 ppm for the peak of acetone.

The fluorine-containing ether compound represented by the formula (1) preferably has a molecular weight dispersity (ratio (Mw/Mn) of weight average molecular weight (Mw) and number average molecular weight (Mn)) of 1.3 or less, by carrying out molecular weight fractionation.

The method of carrying out molecular weight fractionation need not be particularly limited. For example, molecular weight fractionation may be carried out by silica gel column chromatography method, gel permeation chromatography (GPC) method, or the like. Molecular weight fractionation may also be carried out by supercritical extraction method.

"Production Method"

The method for producing the fluorine-containing ether compound of the present embodiment is not particularly limited, and the fluorine-containing ether compound can be produced using a conventionally known production method. The fluorine-containing ether compound of this embodiment can be produced using the method shown below, for example.

For example, a method of reacting a perfluoropolyether compound, having a perfluoropolyether main chain in the molecule and having hydroxy groups at both terminals, with a compound including an epoxy group at one terminal and a cyano group-substituted organic group at the other terminal, may be used. Examples of the compound having an epoxy group at one terminal and a cyano group-substituted organic group at the other terminal include the compounds represented by the following formulas (14) to (20), (34), (40), (45), (47) and (49).

[Chemical Formula 42]

(14)

(15)

(16)

(17)

(18)

(19)

(20)

[Chemical Formula 43]

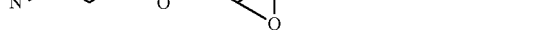
(34)

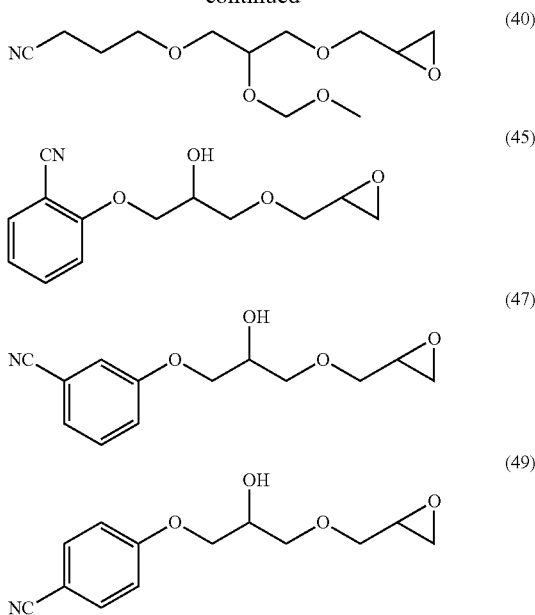

In the fluorine-containing ether compound of the present embodiment, as shown in the above formula (1), a divalent linkage group having a polar group represented by $R^2$ and $R^4$ is linked to both terminals of the PFPE chain represented by $R^3$. A cyano group-substituted organic group is bonded to at least one of them ($R^1$ and/or $R^5$). In the lubricant layer containing the fluorine-containing ether compound of this embodiment, the PFPE chain covers the surface of the protective layer and reduces the frictional force between the magnetic head and the protective layer. It is possible to improve affinity between the lubricant layer containing the fluorine-containing ether compound of the present embodiment and the protective layer by combination of the $R^2$ and $R^4$ arranged at both terminals of the PFPE chain and a cyano group-substituted organic group bonded to at least one of them. As a result, when the lubricant layer is formed on the protective layer of the magnetic recording medium using the lubricant containing the fluorine-containing ether compound of the present embodiment, a lubricant layer in which high coverage rate can be obtained even if the film thickness is small and which has excellent chemical resistance and wear resistance can be formed.

[Lubricant for Magnetic Recording Media]

The lubricant for magnetic recording medium of this embodiment contains a fluorine-containing ether compound represented by the formula (1).

The lubricant of the present embodiment may use one or more known materials as a lubricant material by mixing them as necessary, as long as the known material does not impair the characteristics obtained by containing the fluorine-containing ether compound represented by the formula (1).

Specific examples of known materials include, for example, FOMBLIN (registered trademark) ZDIAC, FOMBLIN ZDEAL, FOMBLIN AM-2001 (the above materials are manufactured by Solvay Solexis), Moresco A20H (manufactured by Moresco) and the like. The known material used in combination with the lubricant of this embodiment preferably has a number average molecular weight of 1000 to 10,000.

When the lubricant of this embodiment contains materials other than the fluorine-containing ether compound represented by formula (1), the amount of the fluorine-containing ether compound represented by formula (1) in the lubricant of this embodiment is preferably 50% by mass or more, and more preferably 70% by mass or more.

Since the lubricant of this embodiment contains the fluorine-containing ether compound represented by the formula (1), the surface of the protective layer can be coated with a high coverage rate even when the thickness is reduced. As a result, a lubricant layer having excellent chemical resistance and wear resistance can be formed.

[Magnetic Recording Medium]

The magnetic recording medium of the present embodiment is obtained by providing at least a magnetic layer, a protective layer, and a lubricant layer sequentially on a substrate.

In the magnetic recording medium of the present embodiment, one or more base layers can be provided between the substrate and the magnetic layer as necessary. Further, an adhesion layer and/or a soft magnetic layer can be provided between the base layer and the substrate.

FIG. 1 is a schematic cross-sectional view showing an embodiment of the magnetic recording medium of the present invention.

The magnetic recording medium 10 of this embodiment has a structure in which an adhesion layer 12, a soft magnetic layer 13, a first base layer 14, a second base layer 15, a magnetic layer 16, a protective layer 17 and a lubricant layer 18 are sequentially provided on a substrate 11.

"Substrate"

As the substrate 11, for example, a nonmagnetic substrate in which a film made of NiP or NiP alloy is formed on a base made of a metal or alloy material such as Al or Al alloy can be used.

The substrate 11 may use a nonmagnetic substrate made of a nonmetallic material such as glass, ceramics, silicon, silicon carbide, carbon, or resin; or may use a nonmagnetic substrate obtained by forming a film made of NiP or NiP alloy on a base made of these nonmetallic materials.

The glass substrate is suitable for increasing the recording density because it has rigidity and excellent smoothness. Examples of the glass substrates include an aluminosilicate glass substrate, and a chemically strengthened aluminosilicate glass substrate, which is particularly preferable.

The roughness of the main surface of the substrate 11 is preferably ultra-smooth with Rmax of 6 nm or less and Ra of 0.6 nm or less. Here, the surface roughness Rmax and Ra are based on the standards of JIS B0601.

"Adhesion Layer"

The adhesion layer 12 prevents the progress of corrosion of the substrate 11 that occurs when the substrate 11 and the soft magnetic layer 13 provided on the adhesion layer 12 are disposed in contact with each other.

The material of the adhesion layer 12 may be appropriately selected from, for example, Cr, Cr alloy, Ti, Ti alloy, CrTi, NiAl, AlRu alloy and the like. The adhesion layer 12 can be formed by, for example, a sputtering method.

"Soft Magnetic Layer"

The soft magnetic layer 13 preferably has a structure in which a first soft magnetic film, an intermediate layer made of a Ru film, and a second soft magnetic film are sequentially stacked. That is, it is preferable that the soft magnetic layer 13 has a structure in which the soft magnetic films above and below the intermediate layer are linked by antiferromagnetic coupling (AFC) by sandwiching the intermediate layer made of a Ru film between the two soft magnetic films.

Examples of the material of the first soft magnetic film and the second soft magnetic film include a CoZrTa alloy and a CoFe alloy.

It is preferable to add any one of Zr, Ta, and Nb to the CoFe alloy used for the first soft magnetic film and the second soft magnetic film. This promotes the amorphization of the first soft magnetic film and the second soft magnetic film, and as a result, it becomes possible to improve the orientation of the first base layer (seed layer) and reduce the floating height of the magnetic head.

The soft magnetic layer 13 can be formed by, for example, a sputtering method.

"First Base Layer"

The first base layer 14 is a layer for controlling the orientation and crystal sizes of the second base layer 15 and the magnetic layer 16 provided on top of the first base layer 14.

Examples of the first base layer 14 include a Cr layer, a Ta layer, a Ru layer, a CrMo alloy layer, a CoW alloy layer, a CrW alloy layer, a CrV alloy layer, and a CrTi alloy layer. The first base layer 14 can be formed by, for example, a sputtering method.

"Second Base Layer"

The second base layer 15 is a layer for turning the magnetic layer 16 to a more favorable orientation. The second base layer 15 is preferably a layer made of Ru or a Ru alloy.

The second base layer 15 may be composed of a single layer or may be composed of a plurality of layers. When the second base layer 15 is composed of a plurality of layers, all the layers may be formed from the same material, or at least one layer may be formed from a different material.

The second base layer 15 can be formed by, for example, a sputtering method.

"Magnetic Layer"

The magnetic layer 16 is made of a magnetic film whose easy magnetization axis is oriented perpendicularly or horizontally to the substrate surface. The magnetic layer 16 is a layer containing Co and Pt, and may be a layer containing an oxide, Cr, B, Cu, Ta, Zr or the like in order to further improve the SNR characteristics.

Examples of the oxide contained in the magnetic layer 16 include $SiO_2$, SiO, $Cr_2O_3$, CoO, $Ta_2O_3$, and $TiO_2$.

The magnetic layer 16 may be composed of one layer, or may be composed of a plurality of magnetic layers made of materials having different compositions.

For example, when the magnetic layer 16 is composed of three layers of a first magnetic layer, a second magnetic layer, and a third magnetic layer that are stacked in order from the bottom, it is preferable that the first magnetic layer has a granular structure that includes a material containing Co, Cr, and Pt and further containing an oxide. As the oxide contained in the first magnetic layer, for example, an oxide of each Cr, Si, Ta, Al, Ti, Mg, and Co is preferably used. Among these, $TiO_2$, $Cr_2O_3$, $SiO_2$ or the like can be preferably used. The first magnetic layer is preferably made of a composite oxide in which two or more types of oxides are added. Of these, $Cr_2O_3$—$SiO_2$, $Cr_2O_3$—$TiO_2$, $SiO_2$—$TiO_2$ or the like can be preferably used.

The first magnetic layer may include at least one element selected from B, Ta, Mo, Cu, Nd, W, Nb, Sm, Tb, Ru, and Re in addition to Co, Cr, Pt, and oxide.

The same material as those used for the first magnetic layer can be used for the second magnetic layer. The second magnetic layer preferably has a granular structure.

The third magnetic layer preferably has a non-granular structure made of a material containing Co, Cr, Pt but containing no oxide. The third magnetic layer may contain one or more elements selected from B, Ta, Mo, Cu, Nd, W, Nb, Sm, Tb, Ru, Re, and Mn in addition to Co, Cr, and Pt.

When the magnetic layer 16 is formed of a plurality of magnetic layers, it is preferable to provide a nonmagnetic layer between adjacent magnetic layers. When the magnetic layer 16 is composed of three layers of the first magnetic layer, the second magnetic layer, and the third magnetic layer, it is preferable to provide a nonmagnetic layer between the first magnetic layer and the second magnetic layer, and between the second magnetic layer and the third magnetic layer.

Examples of materials that can be used favorably for the non-magnetic layers provided between the adjacent magnetic layers of the magnetic layer 16 include Ru, a Ru alloy, a CoCr alloy, and a CoCrX1 alloy (wherein X1 represents one or more elements selected from among Pt, Ta, Zr, Re, Ru, Cu, Nb, Ni, Mn, Ge, Si, O, N, W, Mo, Ti, V and B) and the like.

It is preferable to use an alloy material containing an oxide, a metal nitride, or a metal carbide for the nonmagnetic layer provided between the adjacent magnetic layers of the magnetic layer 16. Specific examples of oxides that may be used include $SiO_2$, $Al_2O_3$, $Ta_2O_5$, $Cr_2O_3$, MgO, $Y_2O_3$, $TiO_2$, and the like. Examples of metal nitrides that may be used include AlN, $Si_3N_4$, TaN, CrN, and the like. Examples of metal carbides that may be used include TaC, BC, SiC, and the like.

The nonmagnetic layer can be formed by, for example, a sputtering method.

The magnetic layer 16 is preferably a magnetic layer for perpendicular magnetic recording in which the easy magnetization axis is oriented in a direction perpendicular to the substrate surface in order to achieve a higher recording density. The magnetic layer 16 may be in-plane magnetic recording.

The magnetic layer 16 may be formed by using any conventionally known method such as a vapor deposition method, an ion beam sputtering method, or a magnetron sputtering method. The magnetic layer 16 is usually formed by a sputtering method.

"Protective Layer"

The protective layer 17 protects the magnetic layer 16. The protective layer 17 may be composed of one layer or may be composed of a plurality of layers. As the protective layer 17, a carbon-based protective layer can be preferably used, and an amorphous carbon protective layer is particularly preferable. It is preferable that the protective layer 17 is a carbon-based protective layer because interaction with a polar group (particularly a hydroxy group) contained in the fluorine-containing ether compound in the lubricant layer 18 is further increased.

The adhesion between the carbon-based protective layer and the lubricant layer 18 can be controlled by making the carbon-based protective layer to contain hydrogenated carbon and/or nitrogenated carbon, and then adjusting the hydrogen content and/or the nitrogen content in the carbon-based protective layer. The hydrogen content in the carbon-based protective layer is preferably 3 to 20 atomic % as measured by the hydrogen forward scattering method (HFS). Further, the nitrogen content in the carbon-based protective layer is preferably 4 to 15 atomic % as measured by X-ray photoelectron spectroscopy (XPS).

The hydrogen and/or nitrogen contained in the carbon-based protective layer need not be uniformly contained in the entire carbon-based protective layer. For example, the carbon-based protective layer is preferably a composition gradient layer in which nitrogen is contained on the lubricant layer 18 side of the protective layer 17 and hydrogen is contained on the magnetic layer 16 side of the protective layer 17. In this case, the adhesion between the magnetic layer 16 and the carbon-based protective layer and the adhesion between the lubricant layer 18 and the carbon-based protective layer are further improved.

The film thickness of the protective layer 17 is preferably 1 nm to 7 nm. When the thickness of the protective layer 17 is 1 nm or more, the performance of the protective layer 17 is sufficiently obtained. The thickness of the protective layer 17 is preferably 7 nm or less from the viewpoint of reducing the thickness of the protective layer 17.

As a method for forming the protective layer 17, a sputtering method using a target material containing carbon, a chemical vapor deposition (CVD) method using a hydrocarbon raw material such as ethylene or toluene, an ion beam deposition (IBD) method, or the like can be used.

When a carbon-based protective layer is formed as the protective layer 17, it can be formed by, for example, a DC magnetron sputtering method. In particular, when a carbon-based protective layer is formed as the protective layer 17, it is preferable to form an amorphous carbon protective layer by plasma CVD. The amorphous carbon protective layer formed by the plasma CVD method has a uniform surface and small roughness.

"Lubricant Layer"

The lubricant layer 18 prevents contamination of the magnetic recording medium 10. Further, the lubricant layer 18 reduces the frictional force of the magnetic head of the magnetic recording/reproducing apparatus that slides on the magnetic recording medium 10, and improves the durability of the magnetic recording medium 10.

The lubricant layer 18 is formed on and is in contact with the protective layer 17, as shown in FIG. 1. The lubricant layer 18 includes the above-described fluorine-containing ether compound.

When the protective layer 17 disposed under the lubricant layer 18 is a carbon-based protective layer, the protective layer 17 is bonded to the fluorine-containing ether compound contained in the lubricant layer 18 with a particularly high bonding strength. As a result, even when the lubricant layer 18 is thin, it is easy to obtain the magnetic recording medium 10 in which the surface of the protective layer 17 is coated with a high coverage rate, and contamination of the surface of the magnetic recording medium 10 can be effectively prevented.

The average film thickness of the lubricant layer 18 is preferably 0.5 nm (5 Å) to 2 nm (20 Å). When the average film thickness of the lubricant layer 18 is 0.5 nm or more, the lubricant layer 18 is formed with a uniform film thickness without forming an island shape or a mesh shape. For this reason, the surface of the protective layer 17 can be covered with the lubricant layer 18 at a high coverage rate. Moreover, by making the average film thickness of the lubricant layer 18 to be 2 nm or less, the lubricant layer 18 can be made sufficiently thin, and the floating height of the magnetic head can be sufficiently reduced.

"Method of Forming Lubricant Layer"

As a method of forming the lubricant layer, for example, a method of preparing a magnetic recording medium in the middle of production in which the layers up to the protective layer 17 are formed on the substrate 11, applying a solution for forming a lubricant layer on the protective layer 17, and then drying the layer, may be used.

The lubricant layer-forming solution can be obtained by dispersing and dissolving the lubricant for magnetic recording medium of the above-described embodiment in a solvent as necessary to obtain a viscosity and concentration suitable for the coating method.

Examples of solvents used in the lubricant layer-forming solution include fluorinated solvents such as Vertrel (registered trademark) XF (trade name, manufactured by Mitsui DuPont Fluorochemical Co., Ltd.).

The method for applying the lubricant layer-forming solution is not particularly limited, and examples thereof include a spin-coating method, a spray method, a paper coating method, and a dip method.

When using the dip method, for example, the following method can be used. First, the substrate 11 on which the layers up to the protective layer 17 are formed is dipped in the lubricant layer-forming solution placed in the dipping tank of the dip coater. Subsequently, the substrate 11 is pulled up from the dipping tank at a predetermined speed. Thus, the lubricant layer-forming solution is applied to the surface of the protective layer 17 on the substrate 11.

By using the dip method, the lubricant layer-forming solution can be applied uniformly to the surface of the protective layer 17, and the lubricant layer 18 can be formed on the protective layer 17 with a uniform film thickness.

In this embodiment, it is preferable to heat the substrate 11 on which the lubricant layer 18 is formed. By performing the heat treatment, the adhesion between the lubricant layer 18 and the protective layer 17 is improved, and the adhesive strength between the lubricant layer 18 and the protective layer 17 is improved.

The heat treatment temperature is preferably 100 to 180° C. When the heat treatment temperature is 100° C. or higher, the effect of improving the adhesion between the lubricant layer 18 and the protective layer 17 is sufficiently obtained. Moreover, thermal decomposition of the lubricant layer 18 can be prevented by setting the heat treatment temperature to 180° C. or lower. The heat treatment time is preferably 10 to 120 minutes.

In this embodiment, in order to further improve the adhesion of the lubricant layer 18 to the protective layer 17, the lubricant layer 18 of the substrate 11 before or after the heat treatment may be subjected to a process of irradiating ultraviolet rays (UV).

The magnetic recording medium 10 of the present embodiment is obtained by sequentially providing at least a magnetic layer 16, a protective layer 17, and a lubricant layer 18 on a substrate 11. In the magnetic recording medium 10 of the present embodiment, the lubricant layer 18 containing the above-mentioned fluorine-containing ether compound is formed on and in contact with the protective layer 17. The lubricant layer 18 has excellent chemical substance resistance and wear resistance even when the thickness is small. Therefore, the magnetic recording medium 10 according to the present embodiment is excellent in reliability, and in particular, is excellent in suppression of silicon contamination and wear resistance. Therefore, the magnetic recording medium 10 of the present embodiment, which has a low magnetic head floating height (for example, 10 nm or less), and which has high reliability that operates stably over a long period of time even in a severe environment due to diversification of applications, can be obtained. For this reason, the magnetic recording medium 10 of this embodiment is particularly suitable as a magnetic disk mounted in a LUL type magnetic disk device.

EXAMPLE

Hereinafter, the present invention will be described more specifically with reference to examples and comparative examples. In addition, this invention is not limited only to the following examples.

Example 1

By the method shown below, the compound represented by the above formula (A) (In the formula (A), m indicating the average degree of polymerization is 4.5 and n indicating the average degree of polymerization is 4.5) was obtained. Hereinafter, the compound represented by the formula (A) is referred to as Compound (A).

First, 2-cyanoethanol and allyl bromide were reacted in tetrahydrofuran in the presence of a base to obtain a compound. Subsequently, the obtained compound was oxidized in dichloromethane using metachloroperbenzoic acid to synthesize a compound represented by the above formula (14).

Next, in a 200 mL eggplant flask under a nitrogen atmosphere, 20 g of a fluoropolyether (number average molecular weight 1000, molecular weight distribution 1.1) represented by $HOCH_2CF_2O(CF_2CF_2O)_h(CF_2O)_iCF_2CH_2OH$ (wherein h indicating an average polymerization degree is 4.5 and i indicating an average polymerization degree is 4.5), 5.59 g of a compound represented by the above formula (14), and 20 mL of t-butanol were charged and stirred at room temperature until uniform.

To this homogeneous solution, 0.90 g of potassium tert-butoxide was added and stirred at 70° C. for 14 hours for reaction. The obtained reaction product was cooled to 25° C., neutralized with 1 mol/L hydrochloric acid, extracted with Vertrel XF (hereinafter sometimes abbreviated as "Vertrel XF") manufactured by Mitsui DuPont Fluorochemical, and washed with water. The organic layer was dehydrated with anhydrous sodium sulfate. After the desiccant was filtered off, the filtrate was concentrated. The residue was purified by silica gel column chromatography to obtain Compound (A).

$^1$H-NMR measurement of the obtained Compound (A) was performed, and the structure was identified from the following results.

$^1$H-NMR (acetone-$D_6$): δ [ppm]=3.40-3.60 (4H), 3.65-3.85 (8H), 3.85-4.10 (10H)

Example 2

By the method shown below, the compound represented by the above formula (B) (in the formula (B), m indicating the average degree of polymerization is 4.5 and n indicating the average degree of polymerization is 4.5) was obtained. Hereinafter, the compound represented by the formula (B) is referred to as Compound (B).

A compound represented by the above formula (15) was synthesized in the same manner as Compound (14) except that lactonitrile was used instead of 2-cyanoethanol.

Then, Compound (B) was obtained in the same manner as in Example 1, except that 5.59 g of the compound represented by the above formula (15) was used instead of the compound represented by the above formula (14) in Example 1.

$^1$H-NMR measurement of the obtained Compound (B) was performed, and the structure was identified by the following results.

$^1$H-NMR (acetone-$D_6$): δ [ppm]=1.60 (6H), 3.65-3.85 (6H), 3.85-4.10 (10H)

Example 3

By the method shown below, the compound represented by the above formula (C) (in the formula (C), m indicating the average degree of polymerization is 4.5 and n indicating the average degree of polymerization is 4.5) was obtained. Hereinafter, the compound represented by the formula (C) is referred to as Compound (C).

A compound represented by the above formula (16) was synthesized in the same manner as Compound (14) except that 3-hydroxybutyronitrile was used instead of 2-cyanoethanol.

Then, Compound (C) was obtained in the same manner as in Example 1, except that 6.21 g of the compound represented by the above formula (16) was used instead of the compound represented by the above formula (14) in Example 1.

$^1$H-NMR measurement of the obtained Compound (C) was performed, and the structure was identified by the following results.

$^1$H-NMR (acetone-$D_6$): δ [ppm]=1.50 (6H), 3.40-3.60 (4H), 3.65-3.85 (6H), 3.85-4.10 (10H)

Example 4

By the method shown below, the compound represented by the above formula (D) (in the formula (D), m indicating the average degree of polymerization is 4.5 and n indicating the average degree of polymerization is 4.5) was obtained. Hereinafter, the compound represented by the above formula (D) is referred to as Compound (D).

A compound represented by the above formula (17) was synthesized in the same manner as Compound (14) except that 3-hydroxyglutaronitrile was used instead of 2-cyanoethanol.

Then, Compound (D) was obtained in the same manner as in Example 1, except that 7.31 g of the compound represented by the above formula (17) was used instead of the compound represented by the above formula (14) in Example 1.

$^1$H-NMR measurement of the obtained Compound (D) was performed, and the structure was identified by the following results.

$^1$H-NMR (acetone-$D_6$): δ [ppm]=3.40-3.60 (8H), 3.65-3.85 (6H), 3.85-4.10 (10H)

Example 5

By the method shown below, the compound represented by the above formula (E) (in the formula (E), m indicating the average degree of polymerization is 4.5 and n indicating the average degree of polymerization is 4.5) was obtained. Hereinafter, the compound represented by the above formula (E) is referred to as Compound (E).

First, the compound represented by the above formula (18) was synthesized by oxidizing allyl cyanoacetate using metachloroperbenzoic acid.

Then, Compound (E) was obtained in the same manner as in Example 1, except that 6.21 g of the compound represented by the above formula (18) was used instead of the compound represented by the above formula (14) in Example 1.

$^1$H-NMR measurement of the obtained Compound (E) was performed, and the structure was identified by the following results.

$^1$H-NMR (acetone-D$_6$): δ [ppm]=3.40-3.60 (4H), 3.75-4.10 (10H)

Example 6

By the method shown below, the compound represented by the above formula (F) (in the formula (F), m indicating the average degree of polymerization is 4.5 and n indicating the average degree of polymerization is 4.5) was obtained. Hereinafter, the compound represented by the formula (F) is referred to as Compound (F).

A compound represented by the above formula (19) was synthesized in the same manner as Compound (14) except that 2-cyanophenol was used in place of 2-cyanoethanol.

Then, Compound (F) was obtained in the same manner as in Example 1, except that 7.71 g of the compound represented by the above formula (19) was used instead of the compound represented by the above formula (14) in Example 1.

$^1$H-NMR measurement of the obtained Compound (F) was performed, and the structure was identified by the following results.

$^1$H-NMR (acetone-D$_6$): δ [ppm]=3.60-3.90 (10H), 4.00-4.10 (4H), 7.00-7.50 (8H)

Example 7

By the method shown below, the compound represented by the above formula (G) (in the formula (G), m indicating the average degree of polymerization is 4.5 and n indicating the average degree of polymerization is 4.5) was obtained. Hereinafter, the compound represented by the above formula (G) is referred to as Compound (G).

First, a compound represented by the following formula (26) was synthesized using 1,3-diallyloxy-2-propanol, pyridine, and paratoluenesulfonyl chloride. Subsequently, the compound represented by the formula (27) was synthesized using the compound represented by the formula (26), trimethylsilylcyanide and tetra-n-butylammonium fluoride. Finally, an epoxy compound represented by the formula (20) was synthesized by oxidizing the compound represented by the formula (27) using metachloroperbenzoic acid.

[Chemical Formula 44]

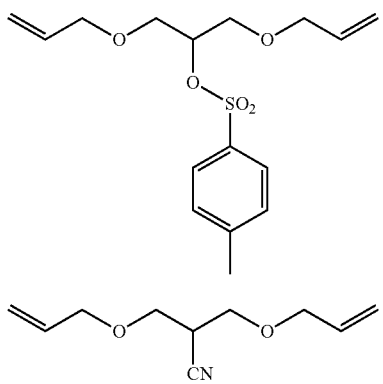

Then, Compound (G) was obtained in the same manner as in Example 1, except that 8.68 g of the compound represented by the above formula (20) was used instead of the compound represented by the above formula (14) in Example 1.

$^1$H-NMR measurement of the obtained Compound (G) was performed, and the structure was identified by the following results.

$^1$H-NMR (acetone-D$_6$): δ [ppm]=3.35~3.65 (12H), 3.65~3.95 (8H), 3.95~4.02 (4H), 4.02~4.15 (4H), 5.05~5.20 (2H), 5.20~5.35 (2H), 5.80~6.00 (2H)

Example 8

By the method shown below, the compound represented by the above formula (H) (in the formula (H), m indicating the average degree of polymerization is 4.5, and n indicating the average degree of polymerization is 4.5) was obtained. Hereinafter, the compound represented by the formula (H) is referred to as Compound (H).

In a 200 mL eggplant flask under a nitrogen atmosphere, 20 g of a fluoropolyether (number average molecular weight 1000, molecular weight distribution 1.1) represented by HOCH$_2$CF$_2$O(CF$_2$CF$_2$O)$_h$(CF$_2$O)$_i$CF$_2$CH$_2$OH (wherein h indicating an average degree of polymerization is 4.5 and i indicating an average degree of polymerization is 4.5), 1.50 g of glycidyl phenyl ether, and 10 mL of t-butanol were charged and stirred at room temperature until uniform.

To this homogeneous solution, 0.90 g of potassium tert-butoxide was added, and the mixture was reacted at 70° C. for 8 hours. The obtained reaction product was cooled to 25° C., neutralized with 0.5 mol/L hydrochloric acid, and then extracted with Vertrel XF. The organic layer was washed with water and dehydrated with anhydrous sodium sulfate. After the desiccant was filtered off, the filtrate was concentrated, and the residue was purified by silica gel column chromatography to obtain 7.25 g of a compound represented by the following formula (21) as an intermediate.

[Chemical Formula 45]

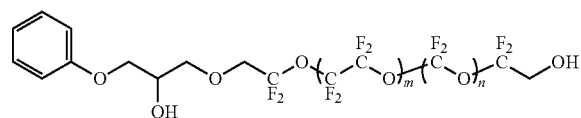

In the formula (21), m indicating the average degree of polymerization is 4.5, and n indicating the average degree of polymerization is 4.5.

In a 200 mL eggplant flask under a nitrogen gas atmosphere, 5.75 g of the compound represented by the above formula (21), 0.763 g of the compound represented by the above formula (14), and 50 mL of t-butanol were charged and stirred at room temperature until uniform.

To this homogeneous solution, 0.187 g of potassium tert-butoxide was added, and the mixture was reacted at 70° C. for 16 hours. The obtained reaction product was cooled to 25° C., neutralized with 0.1 mol/L hydrochloric acid, and extracted with Vertrel XF. The organic layer was washed with water and dehydrated with anhydrous sodium sulfate. After the desiccant was filtered off, the filtrate was concentrated. The residue was purified by silica gel column chromatography to obtain 4.75 g of Compound (H).

$^1$H-NMR measurement of the obtained Compound (H) was performed, and the structure was identified by the following results.

$^1$H-NMR (CD$_3$COCD$_3$): δ [ppm]=3.40-3.60 (2H), 3.65-3.85 (9H), 3.85-4.10 (7H), 6.90-7.10 (5H)

Example 9

By the method shown below, the compound represented by the above formula (I) (in the formula (I), m indicating the average degree of polymerization is 4.5 and n indicating the average degree of polymerization is 4.5) was obtained. Hereinafter, the compound represented by the above formula (I) is referred to as Compound (I).

An epoxy compound represented by the formula (28) was synthesized using thiophene ethanol and epibromohydrin. 4.35 g of Compound (1) was synthesized in the same manner as in Example 8, except that 1.84 g of the epoxy compound represented by the formula (28) was used instead of the phenyl glycidyl ether in Example 8 and the compound represented by the formula (22) was synthesized as an intermediate.

[Chemical Formula 46]

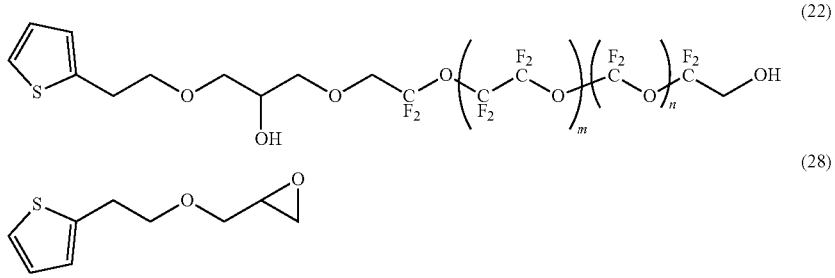

(22)

(28)

In the formula (22), m indicating the average degree of polymerization is 4.5, and n indicating the average degree of polymerization is 4.5.

$^1$H-NMR measurement of the obtained Compound (I) was performed, and the structure was identified from the following results.

$^1$H-NMR (CD$_3$COCD$_3$): δ [ppm]=3.10 (2H), 3.40-3.60 (4H), 3.65-3.85 (9H), 3.85-4.10 (7H), 6.90 (2H), 7.25 (1H)

Example 10

By the method shown below, the compound represented by the above formula (J) (in the formula (J), m indicating the average degree of polymerization is 4.5 and n indicating the average degree of polymerization is 4.5) was obtained. Hereinafter, the compound represented by the formula (J) is referred to as Compound (J).

Then, 4.25 g of Compound (J) was obtained in the same manner as in Example 8, except that 1.14 g of allyl glycidyl ether was used instead of glycidyl phenyl ether and the compound represented by formula (23) was synthesized as an intermediate.

[Chemical Formula 47]

(23)

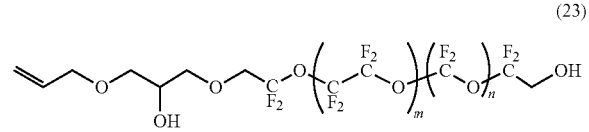

In the formula (23), m indicating the average degree of polymerization is 4.5, and n indicating the average degree of polymerization is 4.5.

$^1$H-NMR measurement of the obtained Compound (J) was performed, and the structure was identified by the following results.

$^1$H-NMR (CD$_3$COCD$_3$): δ [ppm]=3.40-3.60 (2H), 3.60-3.85 (9H), 3.85-4.10 (9H), 5.10-5.20 (1H), 5.20-5.30 (1H), 5.80-6.00 (1H)

Example 11

By the method shown below, the compound represented by the above formula (K) (in the formula (K), m indicating the average degree of polymerization is 4.5 and n indicating the average degree of polymerization is 4.5) was obtained. Hereinafter, the compound represented by the formula (K) is referred to as Compound (K).

A compound represented by the following formula (30) was synthesized using diallyl glycidyl ether, 3,4-dihydro-2H-pyran and p-toluenesulfonic acid. Furthermore, the compound represented by the formula (30) was oxidized using metachloroperbenzoic acid to synthesize the epoxy compound represented by the formula (31).

[Chemical Formula 48]

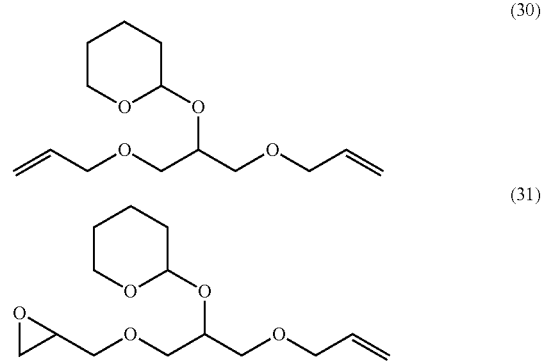

(30)

(31)

In a 200 mL eggplant flask under a nitrogen gas atmosphere, 20 g of a fluoropolyether (number average molecular weight 1000, molecular weight distribution 1.1) represented by HOCH$_2$CF$_2$O(CF$_2$CF$_2$O)$_h$(CF$_2$O)$_i$CF$_2$CH$_2$OH (wherein h indicating an average polymerization degree is 4.5 and i indicating an average polymerization degree is 4.5), 2.72 g of the epoxy compound represented by the formula (31), and 10 mL of t-butanol were charged and stirred at room temperature until uniform. To this homogeneous solution, 0.900 g of potassium tert-butoxide was further added, and the mixture was reacted at 70° C. for 8 hours.

The obtained reaction product was cooled to 25° C., extracted with Vertrel XF, the organic layer was washed with water and dehydrated with anhydrous sodium sulfate. After the desiccant was filtered off, the filtrate was concentrated, and the residue was purified by silica gel column chromatography to obtain 8.01 g of a compound represented by the following formula (24).

[Chemical Formula 49]

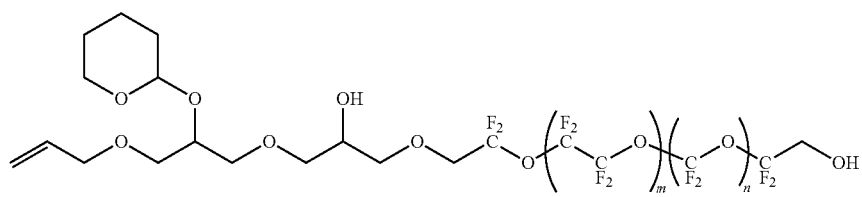

(24)

In the formula (24), m indicating the average degree of polymerization is 4.5, and n indicating the average degree of polymerization is 4.5.

In a 200 mL eggplant flask under a nitrogen gas atmosphere, 6.49 g of the compound represented by the above formula (24), 0.763 g of the compound represented by the above formula (14), and 50 mL of t-butanol were charged and stirred at room temperature until uniform. To this homogeneous solution, 0.187 g of potassium tert-butoxide was added and stirred at 70° C. for 16 hours for reaction.

The obtained reaction product was cooled to 25° C., 20 g of hydrogen chloride methanol solution was added, and the mixture was stirred at 25° C. for 16 hours to be reacted. Then, it was neutralized with saturated sodium hydrogen carbonate aqueous solution, the reaction liquid was extracted with Vertrel XF, the organic layer was washed with water, and was dehydrated with anhydrous sodium sulfate. After the desiccant was filtered off, the filtrate was concentrated. The residue was purified by silica gel column chromatography to obtain 4.90 g of Compound (K).

$^1$H-NMR measurement of the obtained Compound (K) was performed, and the structure was identified by the following results.

$^1$H-NMR (CD$_3$COCD$_3$): δ [ppm]=3.40-3.60 (8H), 3.63-3.82 (6H), 3.84-3.99 (6H), 3.84-3.99 (5H), 5.09-5.12 (1H), 5.23-5.28 (1H), 5.84-5.93 (1H)

Example 12

By the method shown below, the compound represented by the above formula (L) (in the formula (L), m indicating the average degree of polymerization is 4.5 and n indicating the average degree of polymerization is 4.5) was obtained. Hereinafter, the compound represented by the formula (L) is referred to as Compound (L).

Then, 4.28 g of Compound (L) was obtained in the same manner as in Example 10, except that 0.763 g of the compound represented by the above formula (16) was used instead of the compound represented by the above formula (14) in Example 10.

$^1$H-NMR measurement of the obtained Compound (L) was performed, and the structure was identified by the following results.

$^1$H-NMR (acetone-D$_6$): δ [ppm]=1.50 (3H), 3.40-3.85 (12H), 3.85-4.10 (7H), 5.10-5.20 (1H), 5.20-5.30 (1H), 5.80-6.00 (1H)

Example 13

By the method shown below, the compound represented by the above formula (M) (in the formula (M), m indicating the average degree of polymerization is 4.5 and n indicating the average degree of polymerization is 4.5) was obtained. Hereinafter, the compound represented by the formula (M) is referred to as Compound (M).

Then, 4.31 g of Compound (M) was obtained in the same manner as in Example 10, except that 0.997 g of the compound represented by the above formula (17) was used instead of the compound represented by the above formula (14) in Example 10.

$^1$H-NMR measurement of the obtained Compound (M) was performed, and the structure was identified by the following results.

$^1$H-NMR (acetone-D$_6$): δ [ppm]=3.40-3.60 (4H), 3.60-4.10 (17H), 5.10-5.20 (1H), 5.20-5.30 (1H), 5.80-6.00 (1H)

Example 14

By the method shown below, the compound represented by the above formula (N) (in the formula (N), m indicating the average degree of polymerization is 4.5 and n indicating the average degree of polymerization is 4.5) was obtained. Hereinafter, the compound represented by the formula (N) is referred to as Compound (N).

Then, 4.45 g of Compound (N) was obtained in the same manner as in Example 10, except that 0.847 g of the compound represented by the above formula (18) was used instead of the compound represented by the above formula (14) in Example 10.

$^1$H-NMR measurement of the obtained Compound (N) was performed, and the structure was identified by the following results.

$^1$H-NMR (acetone-D$_6$): δ [ppm]=3.40-3.60 (2H), 3.60-4.10 (16H), 5.10-5.20 (1H), 5.20-5.30 (1H), 5.80-6.00 (1H)

Example 15

By the method shown below, the compound represented by the above formula (O) (in the formula (O), m indicating the average degree of polymerization is 4.5, and n indicating the average degree of polymerization is 4.5) was obtained. Hereinafter, the compound represented by the formula (O) is referred to as Compound (O).

Then, 4.58 g of Compound (O) was obtained in the same manner as in Example 10, except that 1.05 g of the compound represented by the above formula (19) was used instead of the compound represented by the above formula (14) in Example 10.

$^1$H-NMR measurement of the obtained Compound (O) was performed, and the structure was identified by the following results.

$^1$H-NMR (acetone-$D_6$): δ [ppm]=3.40-3.60 (2H), 3.60-3.85 (7H), 3.85-4.10 (7H), 5.10-5.20 (1H), 5.20-5.30 (1H), 5.80-6.00 (1H), 6.90-7.40 (4H)

Example 16

By the method shown below, the compound represented by the above formula (P) (in the formula (P), m indicating the average degree of polymerization is 4.5 and n indicating the average degree of polymerization is 4.5) was obtained. Hereinafter, the compound represented by the above formula (P) is referred to as Compound (P).

Then, 4.70 g of Compound (P) was obtained in the same manner as in Example 8, except that 1.18 g of the epoxy compound represented by the above formula (20) was used instead of glycidyl phenyl ether and Compound (25) was synthesized as an intermediate.

[Chemical Formula 50]

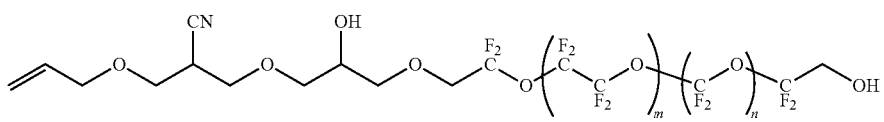

(25)

In the formula (25), m indicating the average degree of polymerization is 4.5, and n indicating the average degree of polymerization is 4.5.

$^1$H-NMR measurement of the obtained Compound (P) was performed, and the structure was identified by the following results.

$^1$H-NMR (acetone-$D_6$): δ [ppm]=3.40-3.60 (8H), 3.63-3.82 (6H), 3.84-3.99 (6H), 3.84-3.99 (5H), 5.09-5.12 (1H), 5.23-5.28 (1H), 5.84-5.93 (1H)

Example 17

By the method shown below, the compound represented by the above formula (Q) (in the formula (Q), m indicating the average degree of polymerization is 4.5 and n indicating the average degree of polymerization is 4.5) was obtained. Hereinafter, the compound represented by the formula (Q) is referred to as Compound (Q).

A compound represented by the following formula (32) was synthesized using ethylene glycol monoallyl ether, 3,4-dihydro-2H-pyran and p-toluenesulfonic acid. Furthermore, the epoxy compound represented by the following formula (33) was synthesized by oxidizing the compound represented by the formula (32) using metachloroperbenzoicacid.

[Chemical Formula 51]

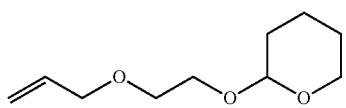

(32)

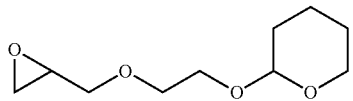

(33)

Then, 4.67 g of Compound (Q) was obtained in the same manner as in Example 16, except that 0.997 g of the epoxy compound represented by the formula (33) was used instead of the compound represented by the above formula (14) in Example 16; the obtained reaction product was cooled to 25° C.; 20 g of a hydrogen chloride methanol solution was added; the mixture was reacted by stirring at 25° C. for 16 hours; and neutralization was performed with a saturated aqueous sodium hydrogen carbonate solution.

$^1$H-NMR measurement of the obtained Compound (Q) was performed, and the structure was identified by the following results.

$^1$H-NMR (acetone-$D_6$): δ [ppm]=3.45-3.58 (9H), 3.62-3.79 (7H), 3.87-4.00 (5H), 4.06-4.18 (5H), 5.10-5.13 (1H), 5.24-5.28 (1H), 5.85-5.94 (1H)

Example 18

By the method shown below, the compound represented by the above formula (R) (in the formula (R), m indicating the average degree of polymerization is 4.5) was obtained. Hereinafter, the compound represented by the formula (R) is referred to as Compound (R).

4.88 g of Compound (R) was obtained in the same manner as in Example 11, except that 20.5 g of fluoropolyether represented by $HOCH_2CF_2CF_2O(CF_2CF_2CF_2O)_h CF_2CF_2CH_2OH$ (wherein h is 4.5) was used instead of the fluoropolyether (number average molecular weight 1000, molecular weight distribution 1.1) represented by $HOCH_2CF_2O(CF_2CF_2O)_h(CF_2O)_iCF_2CH_2OH$ (wherein h representing the average polymerization degree is 4.5 and i representing the average polymerization degree is 4.5) of Example 11.

$^1$H-NMR measurement of the obtained Compound (R) was performed, and the structure was identified by the following results.

$^1$H-NMR ($CD_3COCD_3$): δ [ppm]=3.40-3.60 (8H), 3.63-3.82 (6H), 3.84-3.99 (6H), 3.84-3.99 (5H), 5.09-5.12 (1H), 5.23-5.28 (1H), 5.84-5.93 (1H)

Example 19

By the method shown below, the compound represented by the above formula (V) (in the formula (V), m indicating the average degree of polymerization is 4.5 and n indicating the average degree of polymerization is 4.5) was obtained. Hereinafter, the compound represented by the formula (V) is referred to as Compound (V).

A compound represented by the above formula (34) was synthesized in the same manner as Compound (14) except that 3-cyanopropanol was used instead of 2-cyanoethanol.

Then, Compound (V) was obtained in the same manner as in Example 1, except that 6.21 g of the compound represented by the above formula (34) was used instead of the compound represented by the above formula (14) in Example 1.

$^1$H-NMR and $^{19}$F-NMR measurement of the obtained Compound (V) was performed, and the structure was identified by the following results.

$^1$H-NMR (acetone-D$_6$): δ [ppm]=1.88 (4H), 2.54 (4H), 3.65-3.85 (12H), 3.85-4.10 (8H)

$^{19}$F-NMR (acetone-D$_6$): δ [ppm]=−51.99∼−55.72 (9F), −78.48 (2F), −80.66 (2F), −89.16∼−91.14 (18F)

Example 20

By the method shown below, the compound represented by the above formula (W) (in the formula (W), m indicating the average degree of polymerization is 4.5 and n indicating the average degree of polymerization is 4.5) was obtained. Hereinafter, the compound represented by the formula (W) is referred to as Compound (W).

In a 200 mL eggplant flask under a nitrogen atmosphere, 20 g of a fluoropolyether (number average molecular weight 1000, molecular weight distribution 1.1) represented by the formula HOCH$_2$CF$_2$O (CF$_2$CF$_2$O)$_h$(CF$_2$O)$_i$CF$_2$CH$_2$OH (wherein h indicating an average degree of polymerization is 4.5 and i indicating an average degree of polymerization is 4.5), 1.41 g of the compound represented by the above formula (34), and 10 mL of t-butanol were charged and stirred at room temperature until uniform.

To this homogeneous solution, 0.90 g of potassium tert-butoxide was added, and the mixture was reacted at 70° C. for 8 hours. The obtained reaction product was cooled to 25° C., neutralized with 0.5 mol/L hydrochloric acid, and extracted with Vertrel XF. The organic layer was washed with water and dehydrated with anhydrous sodium sulfate. After the desiccant was filtered off, the filtrate was concentrated, and the residue was purified by silica gel column chromatography to obtain 7.19 g of a compound represented by the following formula (35) as an intermediate.

[Chemical Formula 52]

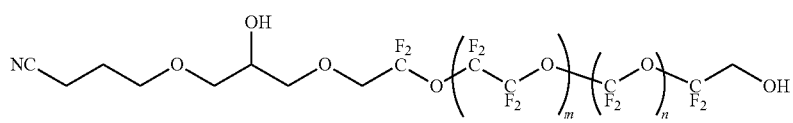

(35)

In the formula (35), m indicating the average degree of polymerization is 4.5, and n indicating the average degree of polymerization is 4.5.

In a 200 mL eggplant flask under a nitrogen gas atmosphere, 5.71 g of the compound represented by the above formula (35), 1.21 g of the compound represented by the above formula (33), and 50 mL of t-butanol were charged and stirred at room temperature until uniform.

To this homogeneous solution, 0.187 g of potassium tert-butoxide was added, and the mixture was reacted at 70° C. for 16 hours. The obtained reaction product was cooled to 25° C., 20 g of a hydrogen chloride methanol solution was added, and the mixture was reacted by stirring at 25° C. for 16 hours, then neutralized with a saturated aqueous sodium hydrogen carbonate solution, and extracted with Vertrel XF. The organic layer was washed with water and dehydrated with anhydrous sodium sulfate. After the desiccant was filtered off, the filtrate was concentrated. The residue was purified by silica gel column chromatography to obtain 4.25 g of Compound (W).

$^1$H-NMR measurement of the obtained Compound (W) was performed, and the structure was identified by the following results.

$^1$H-NMR (acetone-D$_6$): δ [ppm]=1.88 (2H), 2.54 (2H), 3.47-3.80 (15H), 3.85-4.10 (8H)

Example 21

By the method shown below, the compound represented by the above formula (Y) (in the formula (Y), m indicating the average degree of polymerization is 4.5 and n indicating the average degree of polymerization is 4.5) was obtained. Hereinafter, the compound represented by the above formula (Y) is referred to as Compound (Y).

First, a compound represented by the following formula (36) was synthesized using ethylene glycol tert-butyl ether and allyl glycidyl ether. Furthermore, the epoxy compound represented by the following formula (37) was synthesized by oxidizing the compound represented by the formula (36) using metachloroperbenzoic acid.

[Chemical Formula 53]

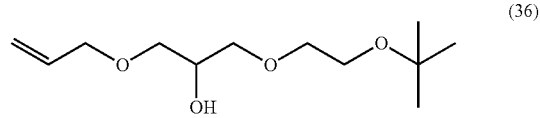
(36)

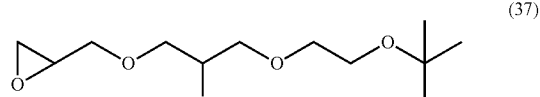
(37)

Then, 4.51 g of Compound (Y) was obtained in the same manner as in Example 20, except that 1.49 g of the compound represented by the above formula (37) was used instead of the compound represented by the above formula (33) in Example 20.

$^1$H-NMR measurement of the obtained Compound (Y) was performed, and the structure was identified by the following results.

$^1$H-NMR (acetone-D$_6$): δ [ppm]=1.88 (2H), 2.54 (2H), 3.47-3.80 (19H), 3.85-4.10 (10H)

Example 22

By the method shown below, the compound represented by the above formula (Z) (in the formula (Z), m indicating the average degree of polymerization is 4.5 and n indicating the average degree of polymerization is 4.5) was obtained. Hereinafter, the compound represented by the formula (Z) is referred to as Compound (Z).

Then, 5.11 g of Compound (Z) was obtained in the same manner as in Example 11, except that 0.847 g of the compound represented by the above formula (34) was used instead of the compound represented by the above formula (14) in Example 11.

$^1$H-NMR measurement of the obtained Compound (Z) was performed, and the structure was identified by the following results.

formula (38), and 10 mL of t-butanol were charged and stirred at room temperature until uniform.

To this homogeneous solution, 0.90 g of potassium tert-butoxide was added, and the mixture was reacted at 70° C. for 8 hours. The obtained reaction product was cooled to 25° C., neutralized with 0.5 mol/L hydrochloric acid, and extracted with Vertrel XF. The organic layer was washed with water and dehydrated with anhydrous sodium sulfate. After the desiccant was filtered off, the filtrate was concentrated. The residue was purified by silica gel column chromatography to obtain 8.21 g of a compound represented by the following formula (39) as an intermediate.

[Chemical Formula 55]

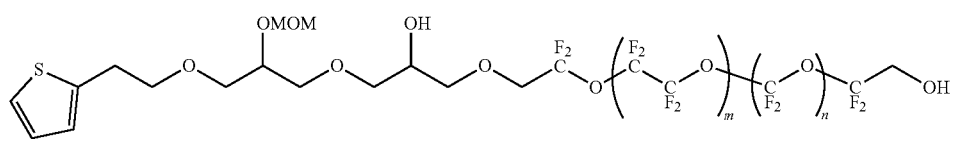

(39)

$^1$H-NMR (acetone-D$_6$): δ [ppm]=1.88 (2H), 2.54 (2H), 3.47-3.80 (14H), 3.85-4.10 (12H), 5.10-5.25 (2H), 5.90 (1H)

Example 23

By the method shown below, the compound represented by the above formula (AA) (in the formula (AA), m indicating the average degree of polymerization is 4.5 and n indicating the average degree of polymerization is 4.5) was obtained. Hereinafter, the compound represented by the formula (AA) is referred to as Compound (AA).

First, a compound represented by the following formula (38) was synthesized by the method shown below. The compound represented by the above formula (28) was hydrolyzed, and the primary hydroxyl group of the obtained compound was protected with a t-butyldimethylsilyl group. Thereafter, the secondary hydroxyl group was protected with a methoxymethyl group, and the t-butyldimethylsilyl group was removed from the resulting compound. The compound represented by the following formula (38) was obtained by reacting epibromohydrin with the resulting primary hydroxyl group.

[Chemical Formula 54]

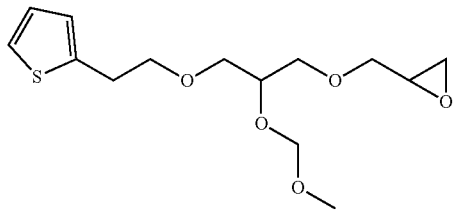

(38)

In a 200 mL eggplant flask under a nitrogen atmosphere, 20 g of a fluoropolyether (number average molecular weight 1000, molecular weight distribution 1.1) represented by formula HOCH$_2$CF$_2$O(CF$_2$CF$_2$O)$_h$(CF$_2$O)$_i$CF$_2$CH$_2$OH (wherein h indicating an average degree of polymerization is 4.5 and i indicating an average degree of polymerization is 4.5), 3.02 g of the compound represented by the above In the formula (39), m indicating the average degree of polymerization is 4.5, and n indicating the average degree of polymerization is 4.5.

In a 200 mL eggplant flask under a nitrogen gas atmosphere, 6.51 g of the compound represented by the above formula (39), 0.847 g of the compound represented by the above formula (34), and 50 mL of t-butanol were charged and stirred at room temperature until uniform.

To this homogeneous solution, 0.187 g of potassium tert-butoxide was added, and the mixture was reacted at 70° C. for 16 hours. The obtained reaction product was cooled to 25° C., 20 g of a hydrogen chloride methanol solution was added, and the mixture was reacted by stirring at 25° C. for 16 hours, then neutralized with a saturated aqueous sodium hydrogen carbonate solution, and extracted with Vertrel XF. The organic layer was washed with water and dehydrated with anhydrous sodium sulfate. After the desiccant was filtered off, the filtrate was concentrated. The residue was purified by silica gel column chromatography to obtain 5.09 g of Compound (AA).

$^1$H-NMR measurement of the obtained Compound (AA) was performed, and the structure was identified by the following results.

$^1$H-NMR (acetone-D$_6$): δ [ppm]=1.88 (2H), 2.54 (2H), 3.05~3.10 (2H), 3.47-3.80 (16H), 3.85-4.10 (10H), 6.90-6.94 (2H), 7.23-7.25 (1H)

Example 24

By the method shown below, the compound represented by the above formula (AB) (in the formula (AB), m indicating the average degree of polymerization is 4.5, and n indicating the average degree of polymerization is 4.5) was obtained. Hereinafter, the compound represented by the formula (AB) is referred to as Compound (AB).

First, the compound represented by the above formula (40) was synthesized by the method shown below. The compound represented by the above formula (34) was hydrolyzed, and the primary hydroxyl group of the obtained compound was protected with a t-butyldimethylsilyl group. Thereafter, the secondary hydroxyl group was protected with a methoxymethyl group, and the t-butyldimethylsilyl group was removed from the resulting compound. The compound represented by the above formula (40) was obtained by reacting epibromohydrin with the resulting primary hydroxyl group.

Then, Compound (AB) was obtained in the same manner as in Example 1, except that 11.4 g of the compound represented by the above formula (40) was used instead of the compound represented by the above formula (14) in Example 1; the obtained reaction product was cooled to 25° C.; 20 g of a hydrogen chloride methanol solution was added; the mixture was reacted by stirring at 25° C. for 16 hours; and the mixture was neutralized with a saturated aqueous sodium hydrogen carbonate solution.

$^1$H-NMR measurement of the obtained Compound (AB) was performed, and the structure was identified by the following results.

$^1$H-NMR (acetone-$D_6$): δ [ppm]=1.88 (4H), 2.54 (4H), 3.47-3.80 (20H), 3.85-4.10 (12H)

Example 25

By the method shown below, the compound represented by the above formula (AC) (in the formula (AC), m indicating the average degree of polymerization is 4.5 and n indicating the average degree of polymerization is 4.5) was obtained. Hereinafter, the compound represented by the above formula (AC) is referred to as Compound (AC).

Then, 4.81 g of Compound (AC) was obtained in the same manner as in Example 20, except that 2.59 g of the epoxy compound represented by the above formula (40) was used instead of the compound represented by the above formula (34) and Compound (41) was synthesized as an intermediate.

[Chemical Formula 56]

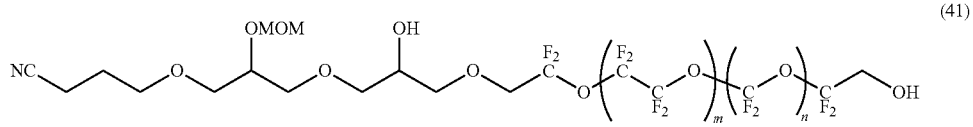

(41)

In the formula (41), m indicating the average degree of polymerization is 4.5, and n indicating the average degree of polymerization is 4.5.

$^1$H-NMR measurement of the obtained Compound (AC) was performed, and the structure was identified by the following results.

$^1$H-NMR (acetone-$D_6$): δ [ppm]=1.88 (2H), 2.54 (2H), 3.47-3.80 (19H), 3.85-4.10 (10H)

Example 26

By the method shown below, the compound represented by the above formula (AD) (in the formula (AD), m indicating the average degree of polymerization is 4.5 and n indicating the average degree of polymerization is 4.5) was obtained. Hereinafter, the compound represented by the above formula (AD) is referred to as Compound (AD).

Then, 5.02 g of Compound (AD) was obtained in the same manner as in Example 25, except that 1.49 g of the epoxy compound represented by the above formula (37) was used instead of the compound represented by the above formula (33).

$^1$H-NMR measurement of the obtained Compound (AD) was performed, and the structure was identified by the following results.

$^1$H-NMR (acetone-$D_6$): δ [ppm]=1.88 (2H), 2.54 (2H), 3.47-3.80 (23H), 3.85-4.10 (12H)

Example 27

By the method shown below, the compound represented by the above formula (AE) (in the formula (AE), m indicating the average degree of polymerization is 4.5, and n indicating the average degree of polymerization is 4.5) was obtained. Hereinafter, the compound represented by the formula (AE) is referred to as Compound (AE).

Then, 5.21 g of Compound (AE) was obtained in the same manner as in Example 11, except that 1.56 g of the compound represented by the above formula (40) was used instead of the compound represented by the above formula (14) in Example 11.

$^1$H-NMR measurement of the obtained Compound (AE) was performed, and the structure was identified by the following results.

$^1$H-NMR (acetone-$D_6$): δ [ppm]=1.88 (2H), 2.54 (2H), 3.47-3.80 (18H), 3.85-4.10 (14H), 5.10-5.25 (2H), 5.90 (1H)

Example 28

By the method shown below, the compound represented by the above formula (AF) (in the formula (AF), m indicating the average degree of polymerization is 4.5 and n indicating the average degree of polymerization is 4.5) was obtained. Hereinafter, the compound represented by the formula (AF) is referred to as Compound (AF).

Then, 5.41 g of Compound (AF) was obtained in the same manner as in Example 23, except that 1.56 g of the compound represented by the above formula (40) was used instead of the compound represented by the above formula (34) in Example 23.

$^1$H-NMR measurement of the obtained Compound (AF) was performed, and the structure was identified by the following results.

$^1$H-NMR (acetone-$D_6$): δ [ppm]=1.88 (2H), 2.54 (2H), 3.05-3.10 (2H), 3.47-3.80 (20H), 3.85-4.10 (12H), 6.90-6.94 (2H), 7.23-7.25 (1H)

Example 29

By the method shown below, the compound represented by the above formula (AG) (in the formula (AG), m indicating the average degree of polymerization is 4.5, and n indicating the average degree of polymerization is 4.5) was obtained. Hereinafter, the compound represented by the formula (AG) is referred to as Compound (AG).

First, a compound represented by the following formula (42) was synthesized using 5-hexen-1-ol, 3,4-dihydro-2H-pyran and p-toluenesulfonic acid. Furthermore, the epoxy compound represented by the following formula (43) was synthesized by oxidizing the compound represented by the formula (42) using metachloroperbenzoic acid.

[Chemical Formula 57]

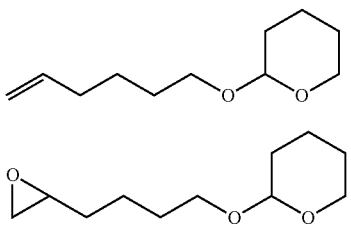

(42)

(43)

Then, 4.92 g of Compound (AG) was obtained in the same manner as in Example 25, except that 1.20 g of the epoxy compound represented by the above formula (43) was used instead of the compound represented by the above formula (33).

$^1$H-NMR measurement of the obtained Compound (AG) was performed, and the structure was identified by the following results.

$^1$H-NMR (acetone-D$_6$): δ [ppm]=1.40-1.60 (6H), 1.88 (2H), 2.54 (2H), 3.47-3.80 (16H), 3.85-4.10 (9H)

Example 30

By the method shown below, the compound represented by the above formula (AH) (in the formula (AH), m indicating the average degree of polymerization is 4.5 and n indicating the average degree of polymerization is 4.5) was obtained. Hereinafter, the compound represented by the formula (AH) is referred to as Compound (AH).

Then, 4.45 g of Compound (AH) was obtained in the same manner as in Example 20, except that 1.75 g of the epoxy compound represented by the above formula (19) was used instead of the compound represented by the above formula (34) and Compound (44) was synthesized as an intermediate.

[Chemical Formula 58]

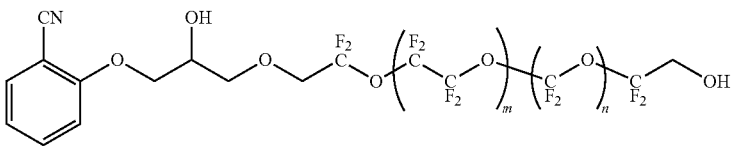

(44)

In the formula (44), m indicating the average degree of polymerization is 4.5, and n indicating the average degree of polymerization is 4.5.

$^1$H-NMR measurement of the obtained Compound (AH) was performed, and the structure was identified by the following results.

$^1$H-NMR (acetone-D$_6$): δ [ppm]=3.47-3.80 (13H), 3.85-4.43 (8H), 7.10 (1H), 7.26 (1H), 7.63 (2H)

Example 31

By the method shown below, the compound represented by the above formula (AI) (in the formula (A), m indicating the average degree of polymerization is 4.5 and n indicating the average degree of polymerization is 4.5) was obtained. Hereinafter, the compound represented by the above formula (AI) is referred to as Compound (A).

First, the compound represented by the above formula (45) was synthesized by the method shown below. A reaction product of 2-cyanophenol and allyl glycidyl ether was oxidized to synthesize a compound represented by the above formula (45).

Then, Compound (A) was obtained in the same manner as in Example 1, except that 11.0 g of the compound represented by the above formula (45) was used instead of the compound represented by the above formula (14) in Example 1.

$^1$H-NMR measurement of the obtained Compound (AI) was performed, and the structure was identified by the following results.

$^1$H-NMR (acetone-D$_6$): δ [ppm]=3.47-3.80 (16H), 3.85-4.43 (12H), 7.10 (2H), 7.26 (2H), 7.63 (4H)

Example 32

By the method shown below, the compound represented by the above formula (AJ) (in the formula (AJ), m indicating the average degree of polymerization is 4.5, and n indicating the average degree of polymerization is 4.5) was obtained. Hereinafter, the compound represented by the formula (AJ) is referred to as Compound (AJ).

Then, 5.01 g of Compound (AJ) was obtained in the same manner as in Example 20, except that 2.49 g of the epoxy compound represented by the above formula (45) was used instead of the compound represented by the above formula (34) and Compound (46) was synthesized as an intermediate.

[Chemical Formula 59]

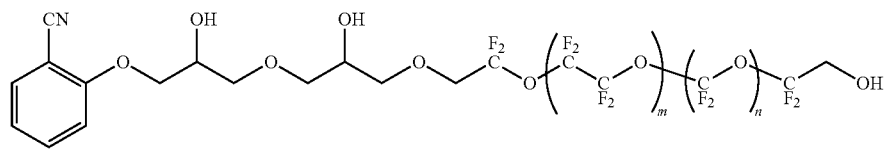

(46)

In the formula (46), m indicating the average degree of polymerization is 4.5, and n indicating the average degree of polymerization is 4.5.

$^1$H-NMR measurement of the obtained Compound (AJ) was performed, and the structure was identified by the following results.

$^1$H-NMR (acetone-$D_6$): δ [ppm]=3.47-3.80 (17H), 3.85-4.43 (10H), 7.10 (1H), 7.26 (1H), 7.63 (2H), Example 33

By the method shown below, the compound represented by the above formula (AK) (in the formula (AK), m indicating the average degree of polymerization is 4.5 and n indicating the average degree of polymerization is 4.5) was obtained. Hereinafter, the compound represented by the formula (AK) is referred to as Compound (AK).

First, the compound represented by the above formula (47) was synthesized by the method shown below. A reaction product of 3-cyanophenol and allyl glycidyl ether was oxidized to synthesize a compound represented by the above formula (47).

Then, 4.99 g of Compound (AK) was obtained in the same manner as in Example 20, except that 2.49 g of the epoxy compound represented by the above formula (47) was used instead of the compound represented by the above formula (34) and Compound (48) was synthesized as an intermediate.

[Chemical Formula 60]

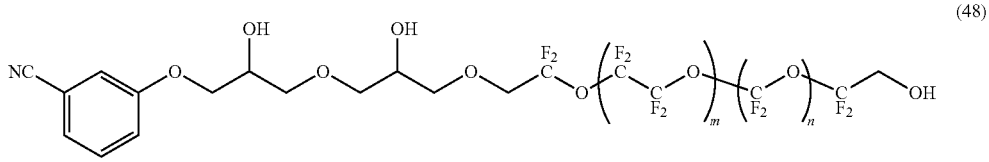

(48)

In the formula (48), m indicating the average degree of polymerization is 4.5, and n indicating the average degree of polymerization is 4.5.

$^1$H-NMR measurement of the obtained Compound (AK) was performed, and the structure was identified by the following results.

$^1$H-NMR (acetone-$D_6$): δ [ppm]=3.47-3.80 (17H), 3.85-4.43 (10H), 7.28-7.34 (3H), 7.50 (1H)

Example 34

By the method shown below, the compound represented by the above formula (AL) (in the formula (AL), m indicating the average degree of polymerization is 4.5 and n indicating the average degree of polymerization is 4.5) was obtained. Hereinafter, the compound represented by the formula (AL) is referred to as Compound (AL).

First, the compound represented by the above formula (49) was synthesized by the method shown below. A reaction product of 4-cyanophenol and allyl glycidyl ether was oxidized to synthesize a compound represented by the above formula (49).

Then, 4.89 g of Compound (AL) was obtained in the same manner as in Example 20, except that 2.49 g of the epoxy compound represented by the above formula (49) was used instead of the compound represented by the above formula (34) and Compound (50) was synthesized as an intermediate.

[Chemical Formula 61]

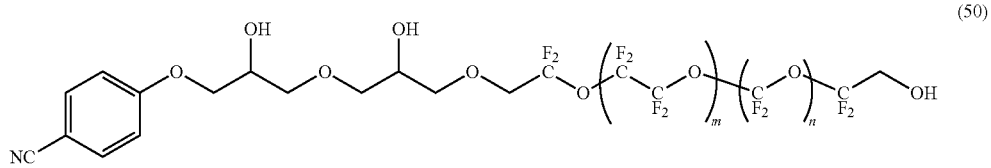

(50)

In the formula (50), m indicating the average degree of polymerization is 4.5, and n indicating the average degree of polymerization is 4.5.

$^1$H-NMR measurement of the obtained Compound (AL) was performed, and the structure was identified by the following results.

$^1$H-NMR (acetone-$D_6$): δ [ppm]=3.47-3.80 (17H), 3.85-4.43 (10H), 7.31 (2H), 7.49 (2H)

Example 35

By the method shown below, the compound represented by the above formula (AM) (in the formula (AM), m indicating the average degree of polymerization is 4.5 and n indicating the average degree of polymerization is 4.5) was obtained. Hereinafter, the compound represented by the formula (AM) is referred to as Compound (AM).

Then, 4.85 g of Compound (AM) was obtained in the same manner as in Example 33, except that 1.49 g of the epoxy compound represented by the above formula (37) was used instead of the compound represented by the above formula (33).

$^1$H-NMR measurement of the obtained Compound (AM) was performed, and the structure was identified by the following results.

$^1$H-NMR (acetone-$D_6$): δ [ppm]=3.47-3.80 (21H), 3.85-4.43 (12H), 7.28-7.34 (3H), 7.50 (1H)

Example 36

By the method shown below, the compound represented by the above formula (AN) (in the formula (AN), m indicating the average degree of polymerization is 4.5 and n indicating the average degree of polymerization is 4.5) was obtained. Hereinafter, the compound represented by the above formula (AN) is referred to as Compound (AN).

Then, 4.75 g of Compound (AN) was obtained in the same manner as in Example 33, except that 0.847 g of the epoxy compound represented by the above formula (34) was used instead of the compound represented by the above formula (33).

$^1$H-NMR measurement of the obtained Compound (AN) was performed, and the structure was identified by the following results.

$^1$H-NMR (acetone-$D_6$): [ppm]=1.88 (2H), 2.54 (2H), 3.47-3.80 (14H), 3.85-4.43 (10H), 7.28-7.34 (3H), 7.50 (1H)

Example 37

By the method shown below, the compound represented by the above formula (AO) (in the formula (AO), m indicating the average degree of polymerization is 4.5 and n indicating the average degree of polymerization is 4.5) was obtained. Hereinafter, the compound represented by the above formula (AO) is referred to as Compound (AO).

Then, 4.95 g of Compound (AO) was obtained in the same manner as in Example 33, except that 1.56 g of the epoxy compound represented by the above formula (40) was used instead of the compound represented by the above formula (33).

$^1$H-NMR measurement of the obtained Compound (AO) was performed, and the structure was identified by the following results.

$^1$H-NMR (acetone-$D_6$): δ [ppm]=1.88 (2H), 2.54 (2H), 3.47-3.80 (18H), 3.85-4.43 (12H), 7.28-7.34 (3H), 7.50 (1H)

Example 38

By the method shown below, the compound represented by the above formula (AP) (in the formula (AP), m indicating the average degree of polymerization is 4.5, and n indicating the average degree of polymerization is 4.5) was obtained. Hereinafter, the compound represented by the formula (AP) is referred to as Compound (AP).

Then, 4.71 g of Compound (AP) was obtained in the same manner as in Example 20, except that 1.56 g of the compound represented by the above formula (40) was used instead of the compound represented by the above formula (33) in Example 20.

$^1$H-NMR measurement of the obtained Compound (AP) was performed, and the structure was identified by the following results.

$^1$H-NMR (acetone-$D_6$): δ [ppm]=1.88 (4H), 2.54 (4H), 3.47-3.80 (16H), 3.85-4.43 (10H)

Example 39

By the method shown below, a compound represented by the above formula (AQ) (in the formula (AQ), m indicating the average degree of polymerization is 4.5) was obtained. Hereinafter, the compound represented by the formula (AQ) is referred to as Compound (AQ).

Then, 4.68 g of Compound (AQ) was obtained in the same manner as in Example 30 except that 20.5 g of a fluoropolyether represented by $HOCH_2CF_2CF_2O(CF_2CF_2CF_2O)_hCF_2CF_2CH_2H$ (where h is 4.5) was used, instead of a fluoropolyether (number average molecular weight 1000, molecular weight distribution 1.1) represented by $HOCH_2CF_2O(CF_2CF_2O)_h(CF_2O)_iCF_2CH_2OH$ (wherein h indicating an average polymerization degree is 4.5 and i indicating an average polymerization degree is 4.5) of Example 30.

$^1$H-NMR and $^{19}$F-NMR measurement of the obtained Compound (AQ) was performed, and the structure was identified by the following results.

$^1$H-NMR (acetone-$D_6$): δ [ppm]=3.53-3.85 (17H), 3.89-4.55 (10H), 7.28-7.34 (3H), 7.50 (1H)

$^{19}$F-NMR (acetone-$D_6$): δ [ppm]=−83.70 (18F), −86.55 (4F), −124.21 (4F), −129.73 (9F)

Example 40

The compound represented by the above formula (AR) (in the formula (AR), m indicating the average degree of polymerization is 7) was obtained by the method shown below. Hereinafter, the compound represented by the formula (AR) is referred to as Compound (AR).

4.58 g of Compound (AQ) was obtained in the same manner as in Example 30, except that 20.0 g of a fluoropolyether represented by $HOCH_2CF_2O(CF_2CF_2O)_hCF_2CH_2OH$ (where h is 7) was used instead of a fluoropolyether (number average molecular weight 1000, molecular weight distribution 1.1) represented by $HOCH_2CF_2O(CF_2CF_2O)_h(CF_2O)_iCF_2CH_2OH$ (wherein h indicating an average polymerization degree is 4.5 and i indicating an average polymerization degree is 4.5) of Example 30.

$^1$H-NMR and $^{19}$F-NMR measurements of the obtained Compound (AR) were performed, and the structure was identified from the following results.

$^1$H-NMR (acetone-$D_6$): δ [ppm]=3.50-3.85 (17H), 3.69-4.43 (10H), 7.28-7.34 (3H), 7.50 (1H)

$^{19}$F-NMR (acetone-$D_6$): δ [ppm]=−78.57 (4F), −89.24~−89.57 (28F)

Comparative Example 1

A compound represented by the following formula (S) was synthesized by the method described in Patent Document 1.

[Chemical Formula 62]

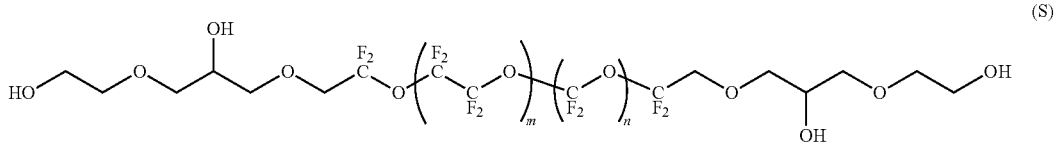

(S)

In the formula (S), m indicating the average degree of polymerization is 4.5, and n indicating the average degree of polymerization is 4.5.

Comparative Example 2

A compound represented by the following formula (T) was synthesized by the method described in Patent Document 2.

[Chemical Formula 63]

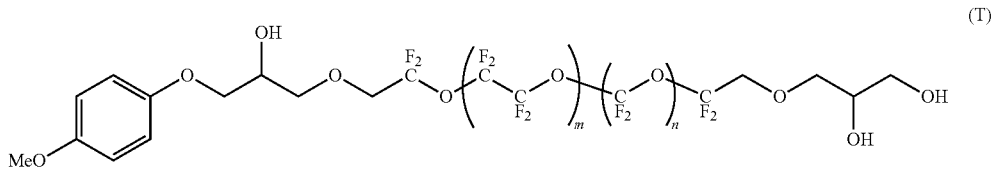

In the formula (T), m indicating the average degree of polymerization is 4.5, and n indicating the average degree of polymerization is 4.5.

Comparative Example 3

A compound represented by the following formula (U) was synthesized by the method described in Patent Document 3.

[Chemical Formula 64]

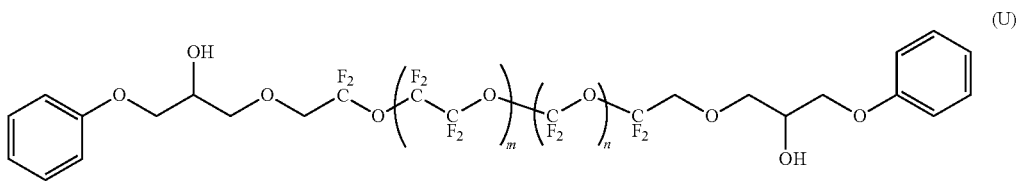

In the formula (U), m indicating the average degree of polymerization is 4.5, and n indicating the average degree of polymerization is 4.5.

The number average molecular weights of the obtained compounds of Examples 1 to 40 and Comparative Examples 1 to 3 were determined by the above-described $^1$H-NMR measurement. The results are shown in Tables 1 and 2.

TABLE 1

| | Compound | Number average molecular weight | Film thickness (Å) | Time Until Coefficient of Friction Sharply Increases (sec) | Si Adsorption amount |
|---|---|---|---|---|---|
| Example 1 | (A) | 1251 | 9.0 | 598 | 0.72 |
| Example 2 | (B) | 1251 | 9.0 | 602 | 0.75 |
| Example 3 | (C) | 1279 | 9.0 | 601 | 0.72 |
| Example 4 | (D) | 1329 | 9.0 | 624 | 0.70 |
| Example 5 | (E) | 1279 | 9.0 | 627 | 0.60 |
| Example 6 | (F) | 1347 | 9.5 | 684 | 0.65 |
| Example 7 | (G) | 1391 | 9.5 | 675 | 0.64 |
| Example 8 | (H) | 1274 | 9.5 | 675 | 0.64 |
| Example 9 | (I) | 1308 | 9.5 | 687 | 0.60 |

TABLE 1-continued

| | Compound | Number average molecular weight | Film thickness (Å) | Time Until Coefficient of Friction Sharply Increases (sec) | Si Adsorption amount |
|---|---|---|---|---|---|
| Example 10 | (J) | 1238 | 9.0 | 661 | 0.59 |
| Example 11 | (K) | 1312 | 9.0 | 650 | 0.52 |
| Example 12 | (L) | 1252 | 9.0 | 649 | 0.64 |
| Example 13 | (M) | 1277 | 9.0 | 629 | 0.60 |
| Example 14 | (N) | 1252 | 9.0 | 633 | 0.61 |
| Example 15 | (O) | 1286 | 9.5 | 680 | 0.60 |
| Example 16 | (P) | 1321 | 9.5 | 680 | 0.60 |
| Example 17 | (Q) | 1312 | 9.5 | 680 | 0.60 |
| Example 18 | (R) | 1362 | 9.0 | 644 | 0.52 |
| Comparative Example 1 | (S) | 1233 | 9.5 | 468 | 1.00 |

TABLE 2

| | Compound | Number average molecular weight | Film thickness (Å) | Time Until Coefficient of Friction Sharply Increases (sec) | Si Adsorption amount |
|---|---|---|---|---|---|
| Example 19 | (V) | 1282 | 9.0 | 610 | 0.72 |
| Example 20 | (W) | 1259 | 9.0 | 602 | 0.60 |
| Example 21 | (Y) | 1333 | 9.0 | 651 | 0.51 |
| Example 22 | (Z) | 1329 | 9.0 | 664 | 0.64 |
| Example 23 | (AA) | 1399 | 9.0 | 689 | 0.69 |
| Example 24 | (AB) | 1430 | 9.0 | 699 | 0.50 |
| Example 25 | (AC) | 1333 | 9.0 | 605 | 0.54 |
| Example 26 | (AD) | 1407 | 9.0 | 692 | 0.48 |
| Example 27 | (AE) | 1403 | 9.0 | 705 | 0.58 |
| Example 28 | (AF) | 1473 | 9.0 | 710 | 0.61 |
| Example 29 | (AG) | 1329 | 9.0 | 620 | 0.68 |
| Example 30 | (AH) | 1293 | 9.0 | 695 | 0.68 |
| Example 31 | (AI) | 1498 | 9.0 | 782 | 0.59 |
| Example 32 | (AJ) | 1367 | 8.5 | 631 | 0.62 |
| Example 33 | (AK) | 1365 | 8.5 | 635 | 0.65 |
| Example 34 | (AL) | 1366 | 8.5 | 642 | 0.67 |
| Example 35 | (AM) | 1441 | 8.5 | 669 | 0.55 |
| Example 36 | (AN) | 1390 | 8.5 | 701 | 0.66 |
| Example 37 | (AO) | 1464 | 8.5 | 727 | 0.55 |
| Example 38 | (AP) | 1356 | 9.0 | 654 | 0.52 |
| Example 39 | (AQ) | 1365 | 9.0 | 643 | 0.65 |
| Example 40 | (AR) | 1365 | 9.0 | 672 | 0.70 |
| Comparative Example 2 | (T) | 1254 | 9.5 | 486 | 1.02 |
| Comparative Example 3 | (U) | 1300 | 9.5 | 492 | 1.10 |

Next, a lubricant layer-forming solution was prepared by using the compounds obtained in Examples 1 to 40 and Comparative Examples 1 to 3 by the method described below. Then, using the obtained lubricant layer-forming solution, a lubricant layer of a magnetic recording medium was formed by the following method, and magnetic recording media of Examples 1 to 40 and Comparative Examples 1 to 3 were obtained.

"Lubricant Layer-Forming Solution"

The compounds obtained in Examples 1 to 40 and Comparative Examples 1 to 3 were each dissolved in Vertrel (registered trademark) XF (trade name, manufactured by Mitsui DuPont Fluoro Chemical Co., Ltd.), which is a fluorine-based solvent, and diluted with Vertrel so that the film thickness would be 8.5 Å to 10 Å when applied onto the protective layer, and a lubricant layer-forming solution of 0.001 to 0.01% by mass was obtained.

"Magnetic Recording Media"

A magnetic recording medium in which an adhesion layer, a soft magnetic layer, a first base layer, a second base layer, a magnetic layer, and a protective layer were sequentially provided on a 65 mm diameter substrate was prepared. The protective layer was made of carbon.

The lubricant layer-forming solutions of Examples 1 to 40 and Comparative Examples 1 to 3 were applied by a dip method on the protective layer of the magnetic recording medium on which the layers up to the protective layer were formed.

Thereafter, the magnetic recording medium coated with the lubricant layer-forming solution was placed in a thermostatic chamber at 120° C. and subjected to heat treatment for 10 minutes. As a result, a lubricant layer was formed on the protective layer to obtain a magnetic recording medium.

The film thicknesses of the lubricant layers of the obtained magnetic recording media of Examples 1 to 40 and Comparative Examples 1 to 3 were measured using FT-IR (trade name: Nicolet iS50, manufactured by Thermo Fisher Scientific). The results are shown in Table 1.

Also, wear resistance tests and chemical substance resistance tests were performed on the magnetic recording media of Examples 1 to 40 and Comparative Examples 1 to 3 by the methods described below. The results are shown in Table 1.

The film thickness of the lubricant layer was determined based on the correlation between the FT-IR method and the ellipsometry method. The main chain of the fluorine-containing ether compound of the present embodiment is mainly formed of C and F. Since the density of C—F in one molecule is different for each type of the compounds, even if the FT-IR peak height is the same, the actual film thickness may be different. Therefore, a disk having each film thickness of 6 to 20 Å (in increments of 2 Å) was prepared, and an increase in film thickness from the disk surface without a lubricant was determined by using an ellipsometer. For these discs, the peak height in C—F stretching vibration was measured using FT-IR, and a correlation equation was obtained from the obtained peak value and the ellipsometer value. By using this correlation equation, the film thickness of the lubricant layers can be easily obtained by the FT-IR measurement.

(Wear Resistance Test)

Using a pin-on-disk type friction and wear tester, an alumina ball having a diameter of 2 mm was used as a contact and was slid on the lubricant layer of the magnetic recording medium with a load of 40 gf at a sliding speed of 0.25 m/sec, to measure a coefficient of friction of the surface of the lubricant layer. The sliding time until the coefficient of friction sharply increases was measured on the surface of the lubricant layer. The sliding time until the coefficient of friction sharply increases was measured four times for the lubricant layer of each magnetic recording medium, and an average value (time) thereof was used as an indicator of the wear resistance of the lubricant coating film.

The time until the coefficient of friction sharply increases can be used as an indicator of the wear resistance of the lubricant layer for the following reason. In the lubricant layer of the magnetic recording medium, wear progresses according to use of the magnetic recording medium. When the lubricant layer disappears due to wear, the contact and the protective layer are in direct contact with each other to cause the coefficient of friction to sharply increase.

As shown in Table 1, the magnetic recording media of Examples 1 to 40 have a longer sliding time until the coefficient of friction increases sharply than the magnetic recording media of Comparative Examples 1 to 3, and have good wear resistance.

It is presumed that this is because in the compound represented by the formula (1) forming the lubricant layer in the magnetic recording media of Examples 1 to 40, at least one of $R^1$ and $R^5$ is an organic group having 1 to 8 carbon atoms wherein one or more hydrogen atoms of the organic group is substituted with a cyano group, and $R^2$ and $R^4$ are divalent linkage groups having a polar group.

(Chemical Resistance Test)

The following evaluation method was used to examine the contamination of magnetic recording media with environmental substances that generate contaminants in a high temperature environment. In the following evaluation method, Si ions were used as the environmental substance, and the amount of Si adsorption was measured as the amount of contaminants that contaminate the magnetic recording medium and that were generated by the environmental substance.

Specifically, the magnetic recording medium to be evaluated was held for 240 hours in the presence of a siloxane-based Si rubber in a high-temperature environment at a temperature of 85° C. and a humidity of 0%. Next, the amount of Si adsorption existing on the surface of the magnetic recording medium was analyzed and measured using secondary ion mass spectrometry (SIMS), and the degree of contamination by Si ions was evaluated based on the amount of Si adsorption. The Si adsorption amount was evaluated using numerical values when the result of Comparative Example 1 was set to 1.00.

From Table 1, it is clear that the magnetic recording media of Examples 1 to 40 have a smaller amount of Si adsorption than the magnetic recording media of Comparative Examples 1 to 3, and are not easily contaminated by environmental substances in a high temperature environment.

DESCRIPTION/EXPLANATION OF REFERENCES

10 . . . Magnetic recording medium,
11 . . . Substrate,
12 . . . Adhesion layer,
13 . . . Soft magnetic layer,
14 . . . First base layer,
15 . . . Second base layer,
16 . . . Magnetic layer,
17 . . . Protective layer,
18 . . . Lubricant layer.

The invention claimed is:

1. A fluorine-containing ether compound represented by the following formula (1), $$R^1—R^2—CH_2—R^3—CH_2—R^4—R^5 \quad (1)$$

wherein in the formula (1), $R^3$ is a perfluoropolyether chain; $R^2$ and $R^4$ are divalent linkage groups represented by the following formula (2-1) and may be the same or different; $R^1$ and $R^5$ are terminal groups bonded to $R^2$ or $R^4$ and may be the same or different; and at least one of $R^1$ and $R^5$ is an organic group having 1 to 8 carbon atoms wherein one or more hydrogen atoms of the organic group is substituted with a cyano group, $$—(X—CH_2CH(OH)CH_2)_a—X— \quad (2-1)$$

wherein in the formula (2-1), a represents an integer of 1 to 3, X represents an oxygen atom or $CH_2$, and two X may be the same or different.

2. The fluorine-containing ether compound according to claim 1, wherein the organic group is a phenyl group or an alkyl group having 1 to 5 carbon atoms.

3. The fluorine-containing ether compound according to claim 1, wherein a in the formula (2-1) is 1 or 2, and each X is an oxygen atom.

4. The fluorinated ether compound according to claim 1, wherein $R^3$ in the formula (1) is any one of the following formulas (3) to (5), $$—CF_2O—(CF_2CF_2O)_c—(CF_2O)_d—CF_2— \quad (3)$$

wherein c and d in the formula (3) represent an average degree of polymerization and each represents 0 to 20, and c or d is 0.1 or more;

$$—CF(CF_3)—(OCF(CF_3)CF_2)_e—OCF(CF_3)— \quad (4)$$

wherein in formula (4), e represents an average degree of polymerization and represents 0.1 to 20; and $$—CF_2CF_2—(OCF_2CF_2CF_2)_f—OCF_2CF_2— \quad (5)$$

wherein in the formula (5) f represents an average degree of polymerization and represents 0.1 to 20.

5. The fluorine-containing ether compound according to claim 1, wherein $R^1$ and $R^5$ in the formula (1) are the same, and $R^2$ and $R^4$ are the same.

6. The fluorine-containing ether compound according to claim 5, wherein $R^1$ and $R^5$ in the formula (1) are alkyl groups having 1 to 5 carbon atoms wherein the alkyl groups are substituted with at least one cyano group.

7. The fluorine-containing ether compound according to claim 1, wherein $R^1$ and $R^5$ in the formula (1) are different, and one of $R^1$ and $R^5$ is a phenyl group substituted with at least one cyano group or an alkyl group having 1 to 5 carbon atoms substituted with at least one cyano group, and the other of $R^1$ and $R^5$ is an organic group having at least one selected from the group consisting of an aromatic ring, a heterocyclic ring, an alkenyl group, an alkynyl group and a hydroxy group.

8. The fluorine-containing ether compound according to claim 1, wherein a number average molecular weight is in the range of 500 to 10,000.

9. A lubricant for magnetic recording media, comprising the fluorine-containing ether compound according to claim 1.

10. A magnetic recording medium in which at least a magnetic layer, a protective layer, and a lubricant layer are sequentially provided on a substrate, wherein the lubricant layer contains the fluorine-containing ether compound according to claim 1.

11. The magnetic recording medium according to claim 10, wherein an average film thickness of the lubricant layer is 0.5 nm to 2 nm.

* * * * *